US010799277B2

(12) United States Patent
Kulper et al.

(10) Patent No.: US 10,799,277 B2
(45) Date of Patent: Oct. 13, 2020

(54) ANTI-PENETRATION BONE IMPLANT DEVICE AND METHOD

(71) Applicant: VERSITECH LIMITED, Hong Kong (CN)

(72) Inventors: Sloan Austin Kulper, Morris Plains, NJ (US); William Weijia Lu, New Territories (CN); Frankie Ka Li Leung, Pok Fu Lam (CN); Christian Xinshuo Fang, Ap Lei Chau (CN)

(73) Assignee: VERSITECH LIMITED, Hong Kong (CN)

( * ) Notice: Subject to any disclaimer, the term of this patent is extended or adjusted under 35 U.S.C. 154(b) by 102 days.

(21) Appl. No.: 15/563,544

(22) PCT Filed: Apr. 1, 2016

(86) PCT No.: PCT/CN2016/078336
§ 371 (c)(1),
(2) Date: Sep. 29, 2017

(87) PCT Pub. No.: WO2016/155665
PCT Pub. Date: Oct. 6, 2016

(65) Prior Publication Data
US 2018/0085154 A1  Mar. 29, 2018

Related U.S. Application Data

(60) Provisional application No. 62/142,207, filed on Apr. 2, 2015.

(51) Int. Cl.
*A61B 17/86* (2006.01)
*A61B 17/70* (2006.01)
(Continued)

(52) U.S. Cl.
CPC .......... *A61B 17/86* (2013.01); *A61B 17/0401* (2013.01); *A61B 17/7001* (2013.01);
(Continued)

(58) Field of Classification Search
CPC ... A61B 17/86; A61B 17/844; A61B 17/0401; A61B 17/0412; A61B 2017/0437
See application file for complete search history.

(56) References Cited

U.S. PATENT DOCUMENTS

| 5,707,395 A | * | 1/1998 | Li | A61B 17/0401 606/232 |
| 2004/0002735 A1 | * | 1/2004 | Lizardi | A61B 17/0401 606/232 |

(Continued)

FOREIGN PATENT DOCUMENTS

| CN | 102639073 A | 8/2012 |
| CN | 102824207 A | 12/2012 |

(Continued)

OTHER PUBLICATIONS

Maynard, et al., Attorney Arguments/Remarks (Year: 2020).*
(Continued)

Primary Examiner — Christian A Sevilla
(74) Attorney, Agent, or Firm — Joseph G. Chu; Jeremy I. Maynard; JCIP

(57) ABSTRACT

A device for engagement with a bone includes a dynamically expandable tip (12), a dynamically expandable ring (40), or other dynamically expandable insert (60, 62, 401L) that reacts to forces pushing the implant into bone tissue. The tip (12), ring (40) or insert (60, 62, 401L) expands at least normal to the direction of motion, increasing contact area between the surrounding bone tissue and the material and thereby reducing the occurrence of high areas of contact stress in the adjacent bone tissue. The tip (12), ring (40) or (Continued)

insert (60, 62, 401L) translates forces along an axis of motion into lateral frictional forces that can resist penetration into the bone tissue without the need for additional operator or patient interaction. A method of reducing migration of the device for engagement includes the steps of providing the device and inserting the device within bone tissue.

20 Claims, 32 Drawing Sheets

(51) Int. Cl.
    *A61B 17/04*     (2006.01)
    *A61B 17/84*     (2006.01)
    *A61B 17/00*     (2006.01)

(52) U.S. Cl.
    CPC ........ *A61B 17/844* (2013.01); *A61B 17/8625* (2013.01); *A61B 17/8635* (2013.01); *A61B 2017/00858* (2013.01); *A61B 2017/00862* (2013.01); *A61B 2017/042* (2013.01); *A61B 2017/044* (2013.01); *A61B 2017/0429* (2013.01); *A61B 2017/0432* (2013.01); *A61B 2017/0437* (2013.01); *A61B 2017/8655* (2013.01)

(56) References Cited

U.S. PATENT DOCUMENTS

| | | |
|---|---|---|
| 2006/0122622 A1 | 6/2006 | Truckai et al. |
| 2006/0282081 A1* | 12/2006 | Fanton ............... A61B 17/0401 606/232 |
| 2007/0270858 A1* | 11/2007 | Trieu ................. A61B 17/7098 606/279 |
| 2009/0099610 A1* | 4/2009 | Johnson ............. A61B 17/7055 606/86 R |
| 2009/0125028 A1 | 5/2009 | Teisen et al. |
| 2010/0217325 A1* | 8/2010 | Hochschuler ........ A61B 17/864 606/264 |
| 2011/0004256 A1* | 1/2011 | Biedermann ...... A61B 17/7098 606/301 |
| 2012/0109222 A1 | 5/2012 | Goel et al. |
| 2013/0226251 A1 | 8/2013 | Chegini et al. |
| 2014/0094860 A1 | 4/2014 | Reimels |

FOREIGN PATENT DOCUMENTS

| | | |
|---|---|---|
| CN | 202723963 U | 2/2013 |
| WO | 2010118052 A1 | 10/2010 |

OTHER PUBLICATIONS

Written Opinion and International Search Report of PCT/CN2016/078336.
Supplementary European Search Report of EP 16 77 1420.
Chinese Office Action for Application No. 201680019612.2.

\* cited by examiner

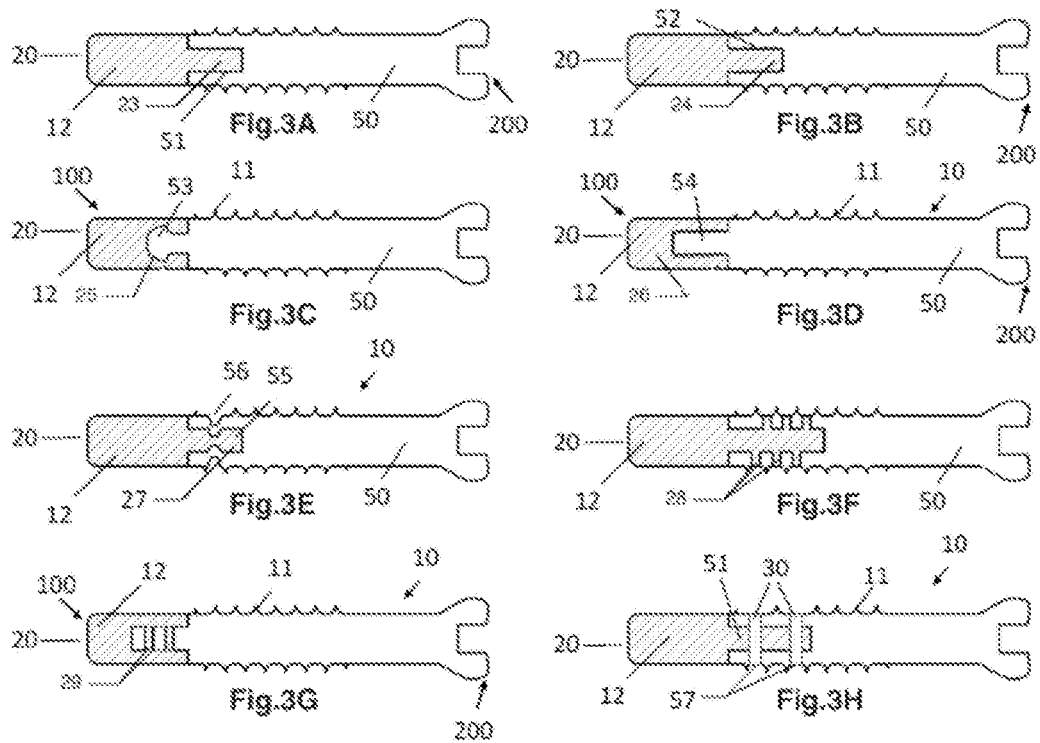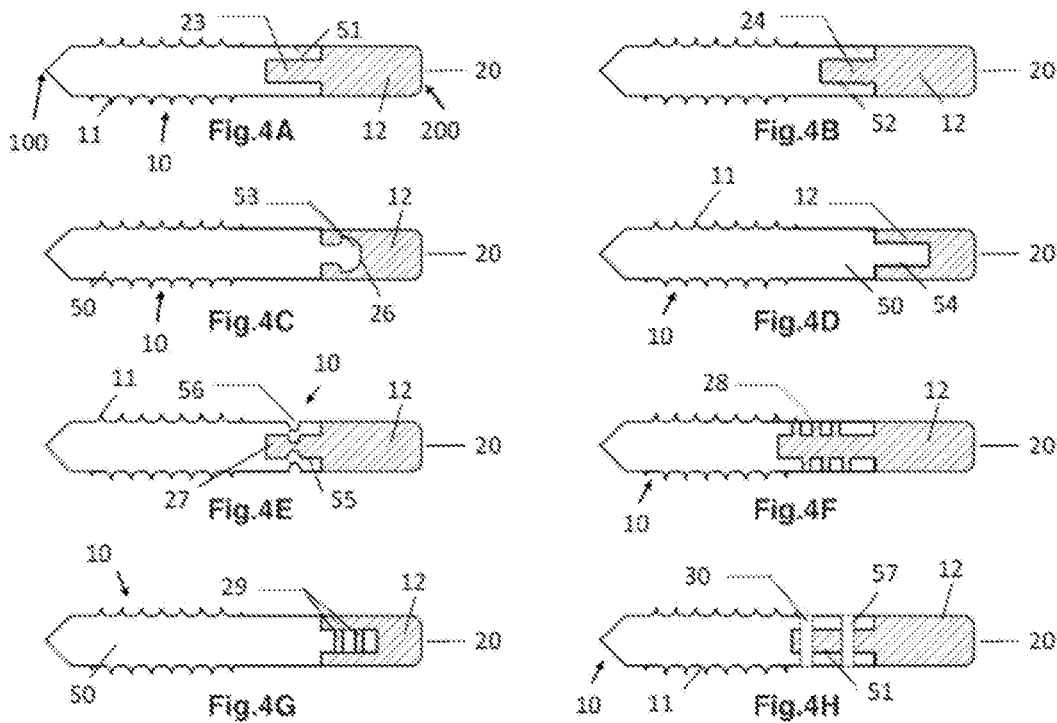

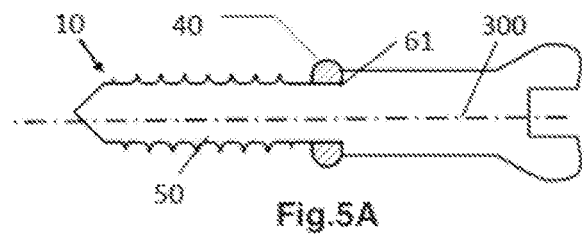
Fig.5A
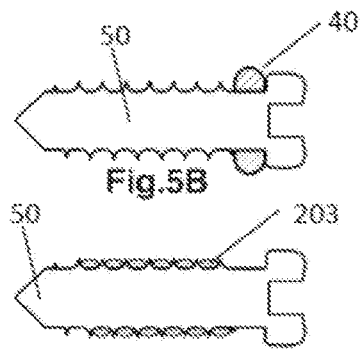
Fig.5B
Fig.5C
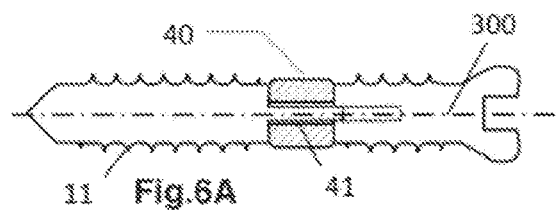
Fig.6A
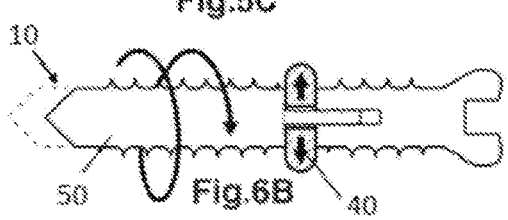
Fig.6B
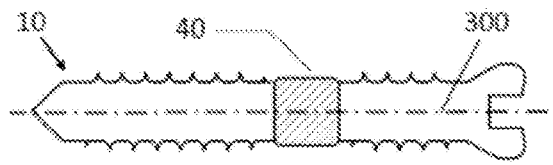
Fig.7A
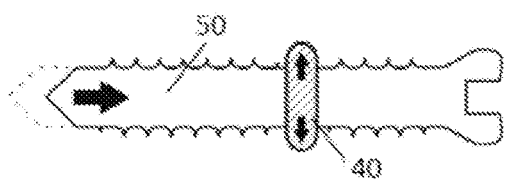
Fig.7B
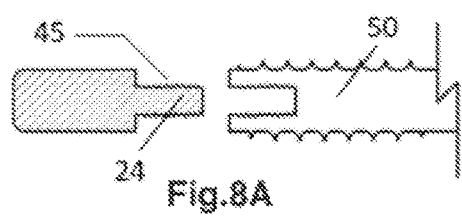
Fig.8A
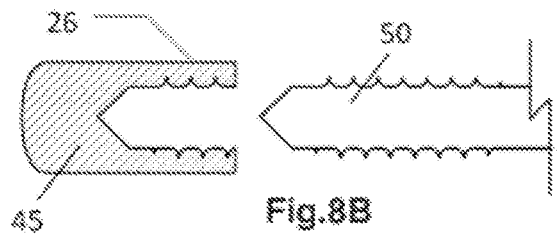
Fig.8B

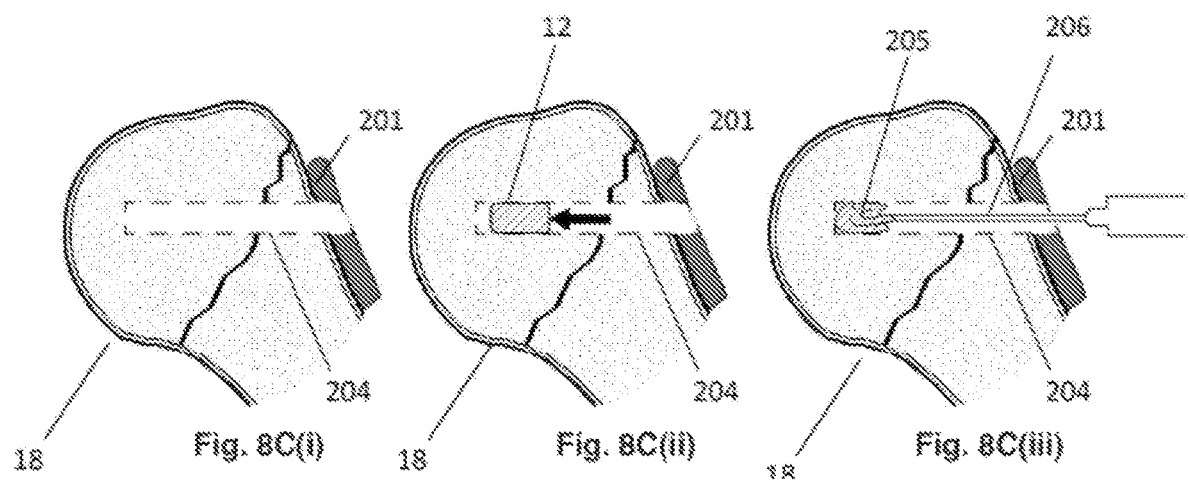
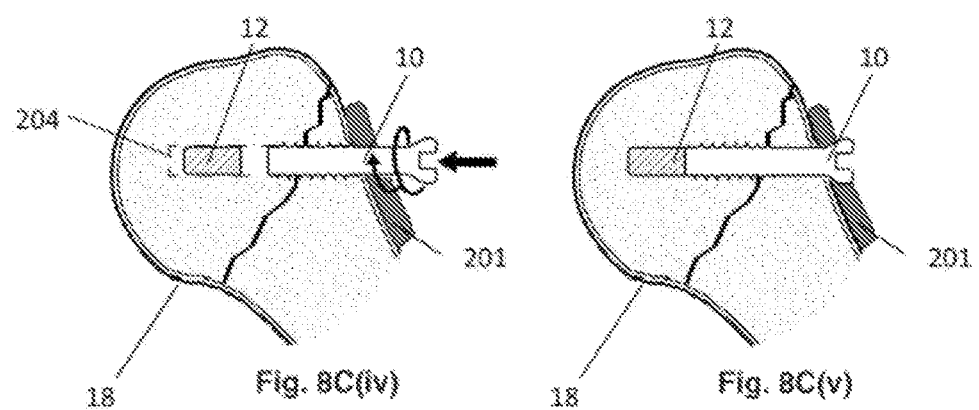

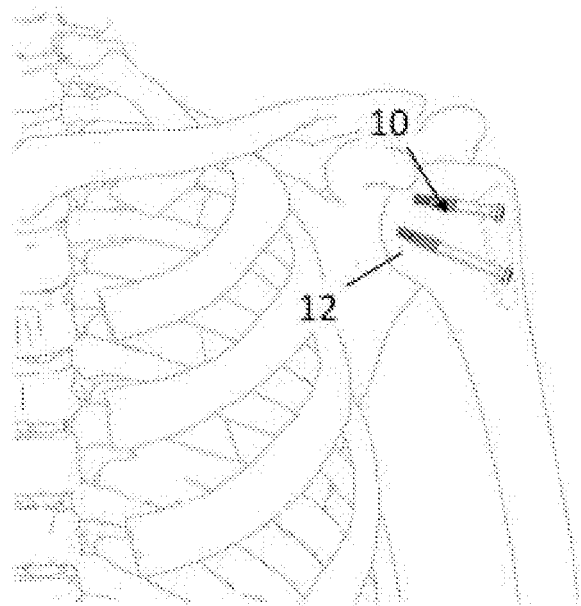
Fig.13C
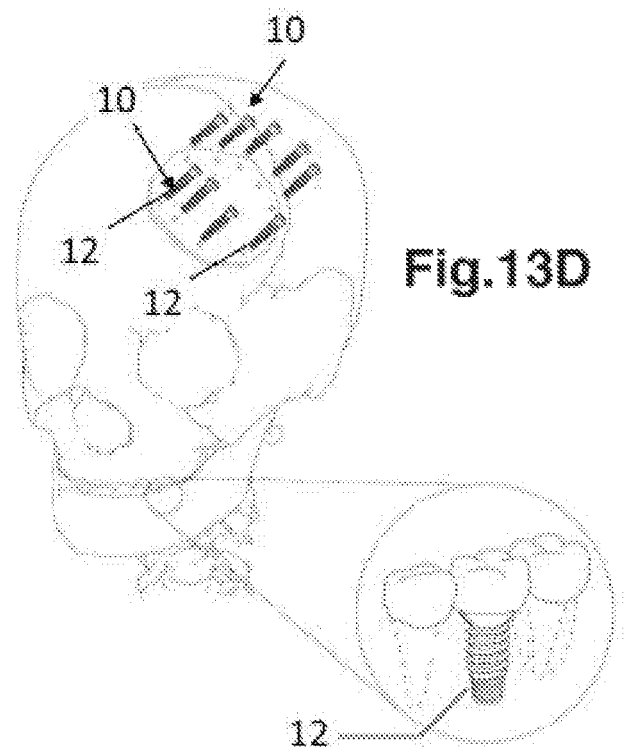
Fig.13D
Fig.13E

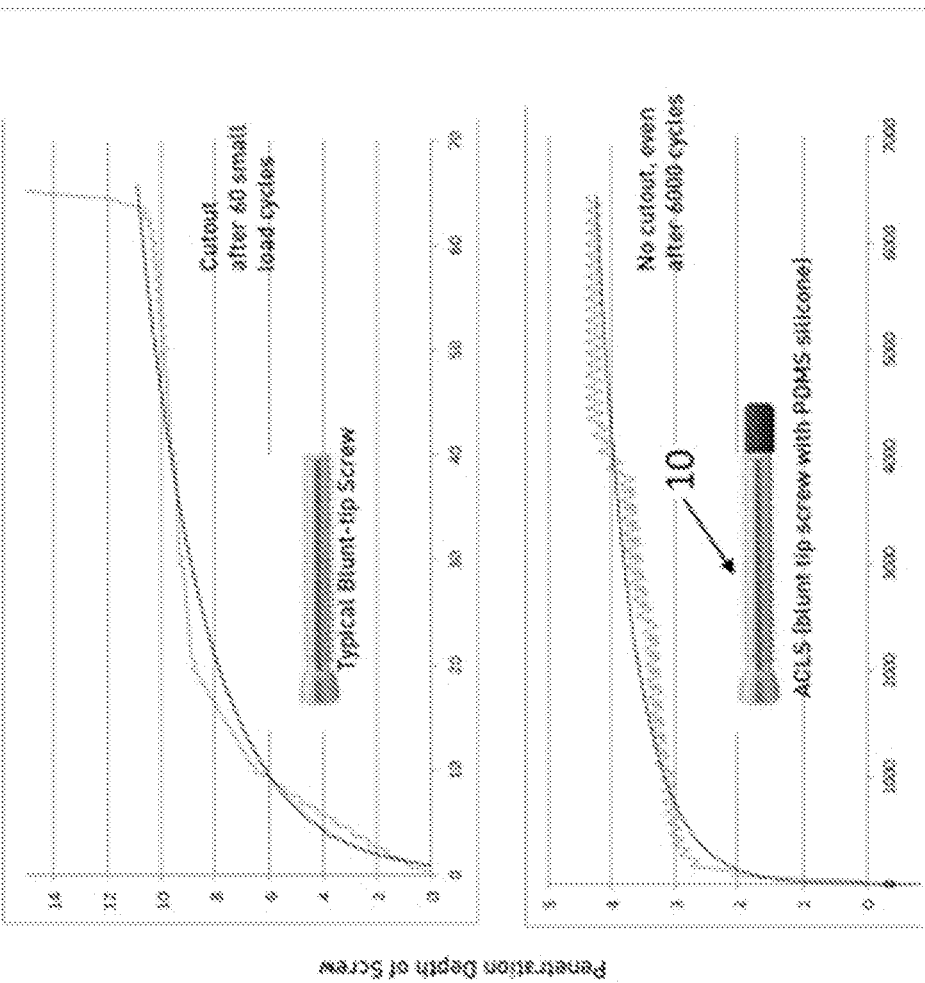
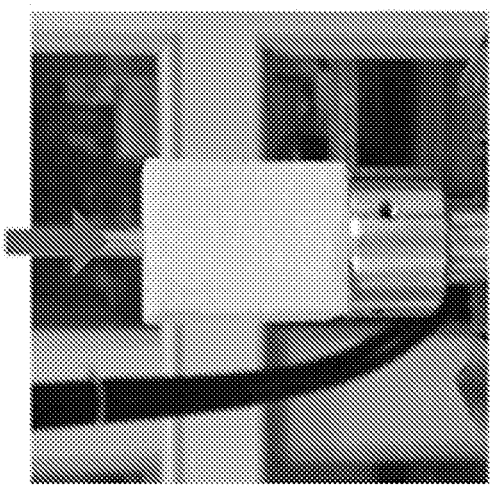
Fig. 15B

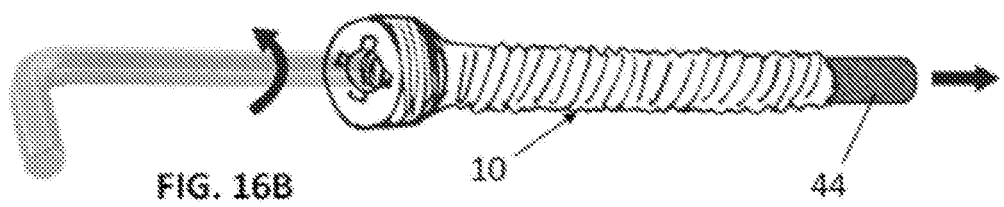
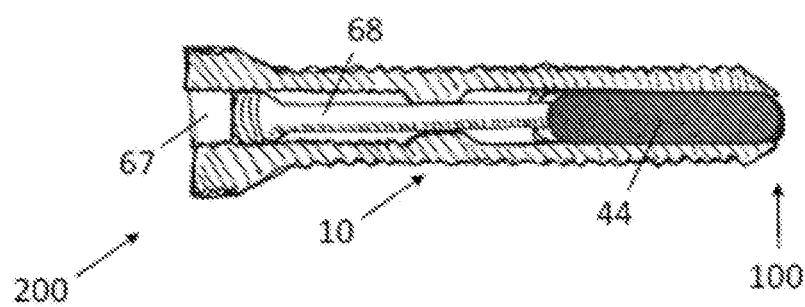
FIG. 16B
FIG. 16A

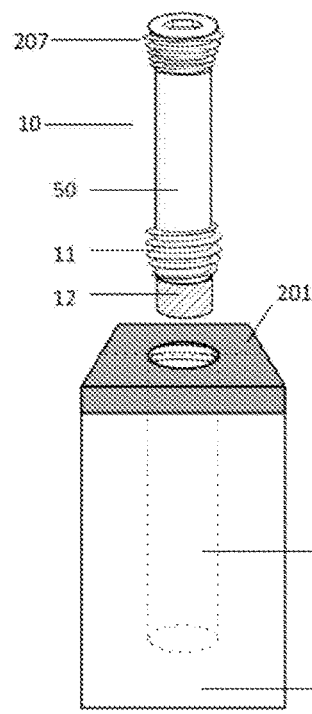
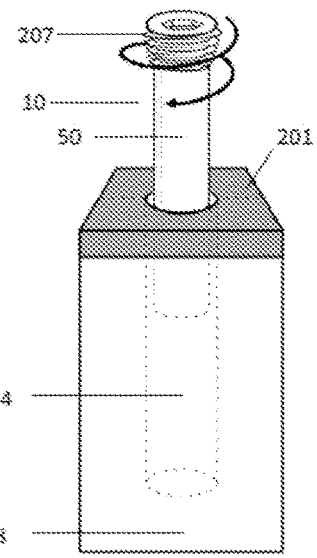
Fig. 17A  Fig. 17B
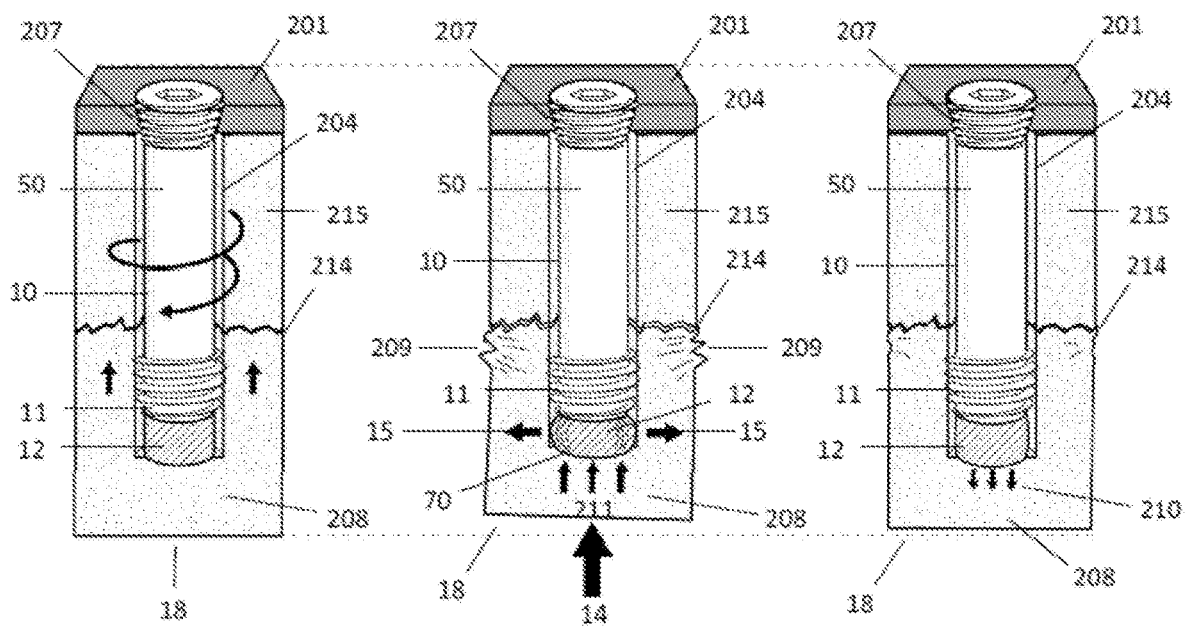
Fig. 17C(i)   Fig. 17C(ii)   Fig. 17C(iii)

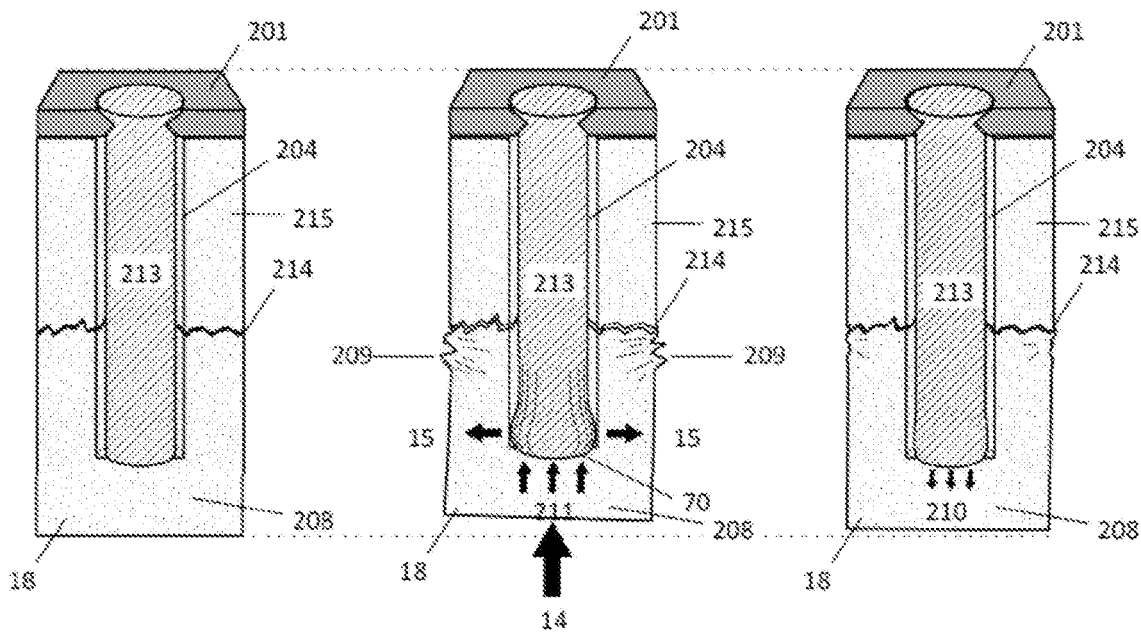
Fig. 21A(i)　　　Fig. 21A(ii)　　　Fig. 21A(iii)
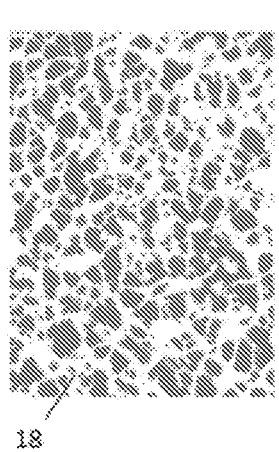
Fig. 22A
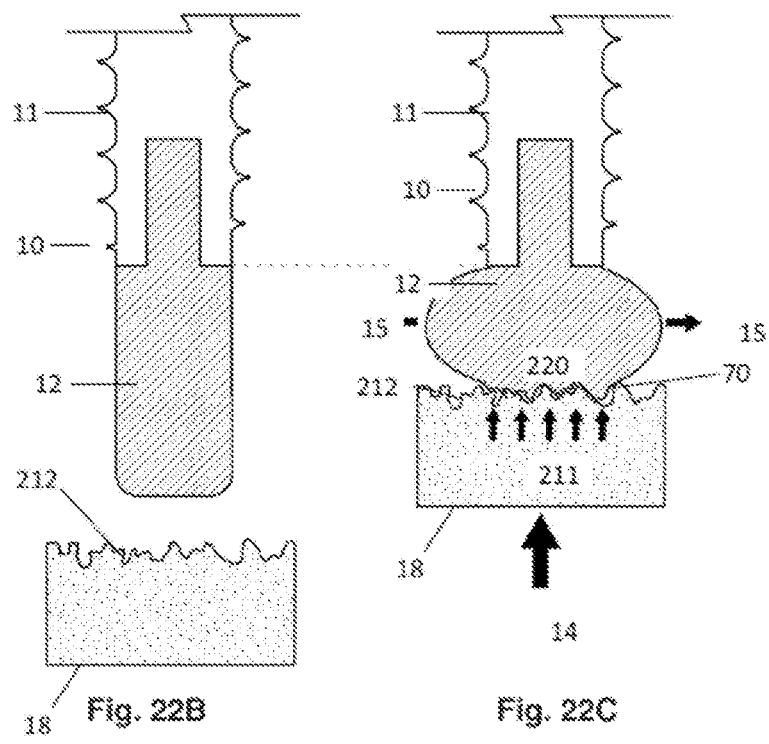
Fig. 22B　　　Fig. 22C

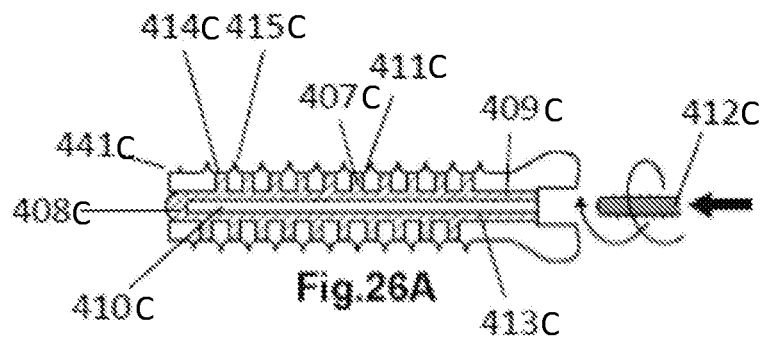
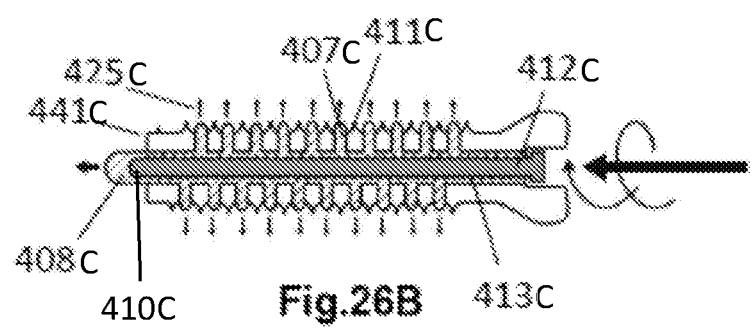
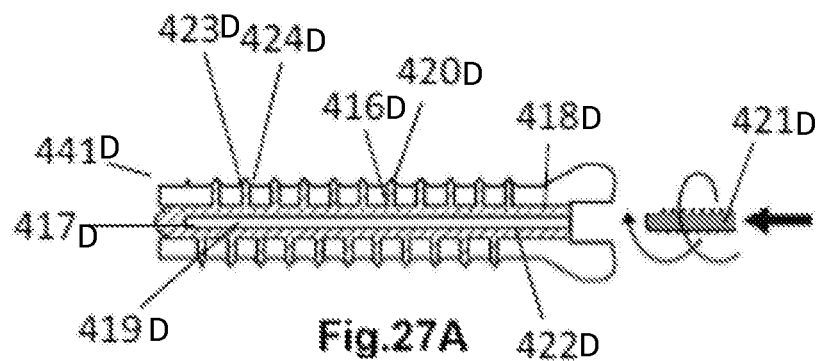
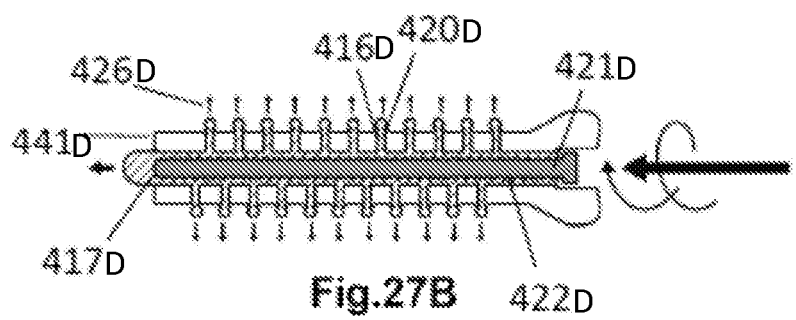

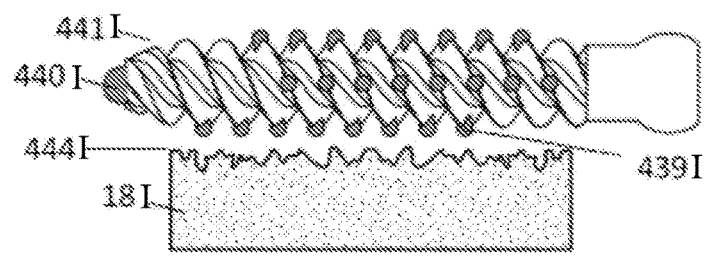
Fig.32A
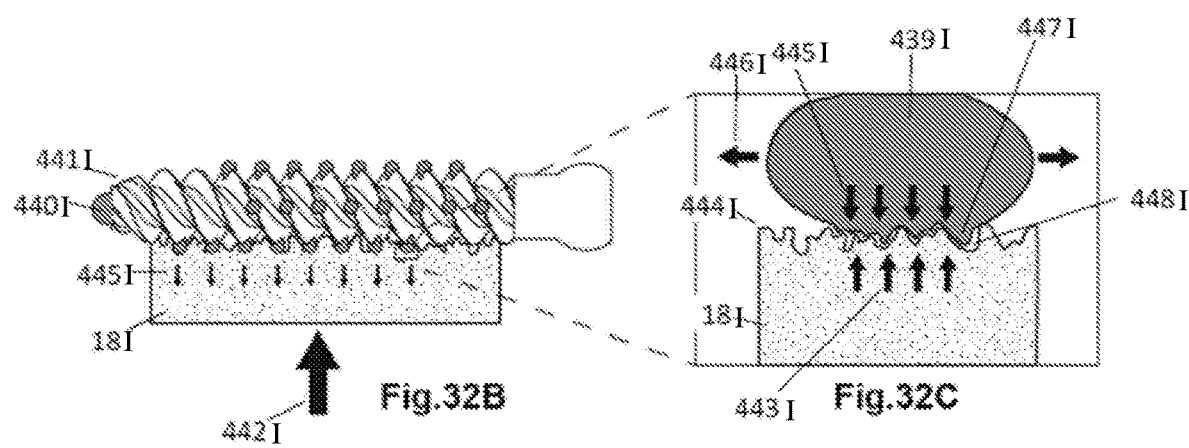
Fig.32B
Fig.32C

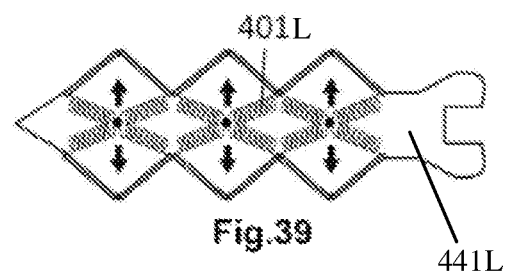
Fig. 39
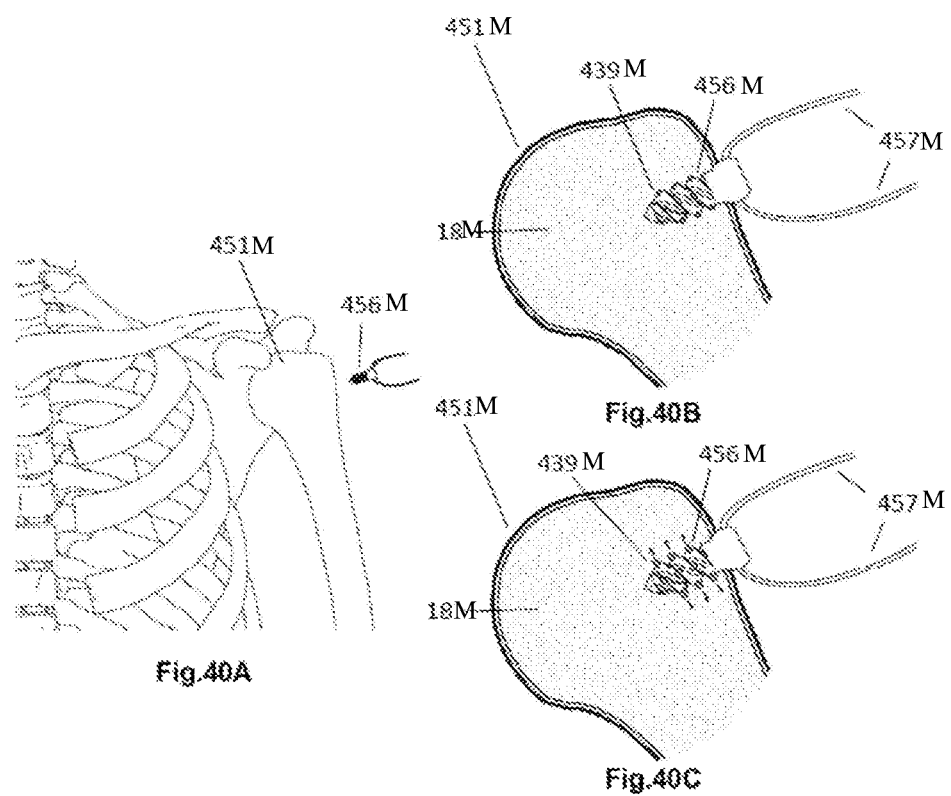
Fig. 40A
Fig. 40B
Fig. 40C

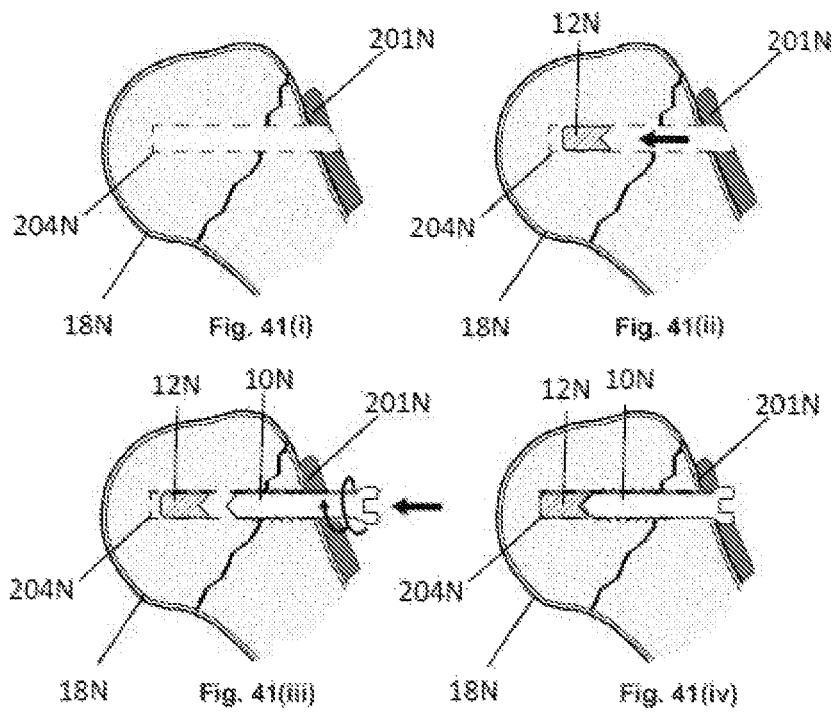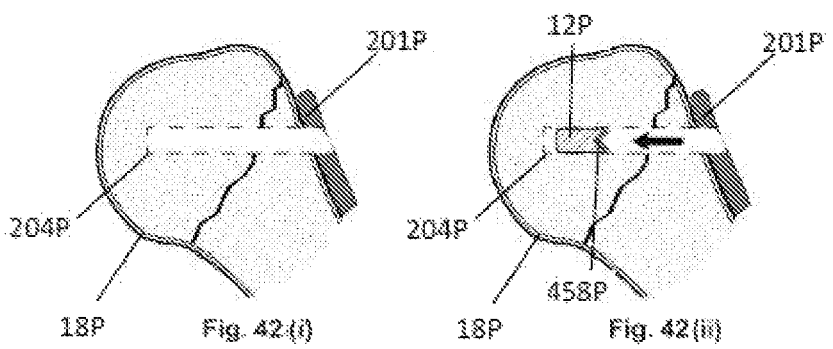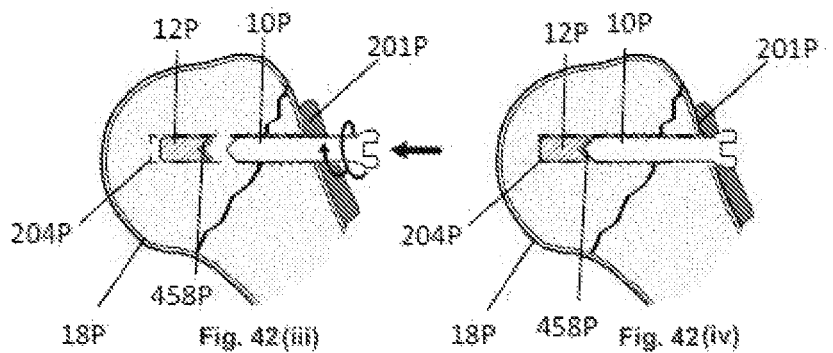

ANTI-PENETRATION BONE IMPLANT DEVICE AND METHOD

BACKGROUND OF THE INVENTION

There exist numerous problems related to the biomechanical and biological properties of bone which may potentially reduce the ability of implants, such as orthopaedic implants, to satisfactorily treat musculoskeletal injuries, trauma and defects. By way of example, implants such as bone screws, nails, and plates may weaken surrounding tissue through a mechanism known as stress shielding. In the case of another mechanism known as aseptic loosening, the fit between orthopedic implants and bone tissue may become looser over time as loading on the implant crushes and compacts adjacent bone tissue. During progressive cut out, an implant gradually penetrates through the bone until it breaks through the cortex entirely. Such biomechanical problems are often related to, and exacerbated by, biological changes to the processes of bone generation and remodeling. One common biological change is the loss of bone mass and structural strength due to imbalance in the bone remodeling process, a condition known as osteopenia, or its more extreme form, osteoporosis.

As global life expectancies have risen during the $21^{st}$ century, an increasing number of otherwise healthy and able elderly people have suffered from painful and debilitating fractures due to osteoporosis. Fractures of the hip, shoulder and spine are especially prevalent due to the relatively high content of cancellous, or "spongy," tissue within the larger, load-bearing bones. In individuals with osteoporosis, these bones often develop numerous cavities and cysts within the spongy tissue that can compromise structural strength and lead to higher fracture rates.

A common form of treatment for such fractures is surgical fixation via the implantation of metal rods or screws that secure bone fragments in their original anatomical positions during the healing process. Osteoporotic bone, however, has a highly porous interior that is often too structurally weak and inadequate for the secure attachment of implant screws or other similar fixation devices. Patients with osteoporosis who undergo internal fracture fixation often experience a complication known as "cut-out," in which natural movement, bone shrinkage, or accidental injury can cause an implant screw or other embedded fixation device to penetrate through the bone and out into surrounding soft tissues. In the case of the hip, shoulder, or spine, this frequently leads to severe trauma of the articular cartilage of the joint or intervertebral disc and requires surgical revision to correct.

Furthermore, all bone tissue, in particularly bone tissue already weakened by conditions such as osteoporosis, degenerative disorders, compromised bone stock, are susceptible to complications due to the migration and loosening of devices including implants, fixation devices and bone anchors.

Such migration of the device within the bone can cause instability of fracture site, aseptic loosening, increased stresses on implants and fixation devices which may precipitate fatigue and failure and upon bone anchors which may cause instability and potential loosening and pull-out, and other complications that reduce overall musculoskeletal health and integrity of bone tissue and bone stability. As mentioned above, the presence of a device within bone stock may contribute to or cause weakness of the bone through mechanisms such as bone resorption due to stress shielding.

The majority of prior attempts to create implant screws and other fixation devices with an improved ability to remain stationary within bone tissue have focused on the use of rigid mechanisms that firmly anchor implants to the surrounding bone tissue. Examples of such mechanisms include expanding metal sleeves, articulated arms, and telescoping fingers designed to penetrate into and grab hold of bone tissue. Additionally, many examples in the prior art focus on preventing the pull out, or removal, of the implant screw, rather than improved penetration into the bone tissue as emphasized by the current invention.

BRIEF SUMMARY OF THE INVENTION

The embodiments of the subject invention successfully address the above-described disadvantages associated with the previously known devices and methods, and provide certain attributes and advantages, which have not been realized by these known devices. In particular, the subject invention provides a novel, inexpensive, and highly effective improvement to bone implant devices, such as bone screws, that inhibit "cut-out" or bone penetration often experienced with other types of implant screws and implant fixation devices. The subject invention also reduces migration of fixation, implants and bone anchors within and relative to bone tissue, which reduces other complications related to the unwanted penetration or migration of bone relative to an implant and to other bone in the case of fracture fixation and reduction, such as caused by localised stress concentration near the implant, which is known to cause complications including aseptic loosening, implant instability and potential failure and bone resorption due to stress shielding.

The embodiments of the current invention are applicable to bone implants and/or methods of improving existing bone implants. In particular, embodiments of the subject invention provide an improved bone screw that can inhibit the undesirable penetration of the bone screw through the bone tissue and into the soft tissue around the bone tissue following implantation. Following implantation into bone tissue, the implant can dynamically react to forces pushing the bone screw into the bone tissue by deforming such that contact area between the surrounding bone tissue and the material is increased, thereby reducing the occurrence of high areas of contact stress in the adjacent bone tissue. In particular, the deformation behavior of the current invention may permit expansion into the pores and cavities present in osteoporotic cancellous bone tissue, thereby further increasing the contact area between implant and bone tissue. Simultaneously, the implant has the additional behavior of translating forces along an axis of motion into lateral frictional forces that can resist penetration into the bone tissue without the need for additional operator or patient interaction. Following removal of loading forces pushing the bone screw into the bone tissue, the implant can return to its un-deformed state.

Embodiments include dynamically expanding structures of elastomeric polymer materials and/or dynamically expanding mechanisms designed to approximate the mechanical behavior of such elastomeric polymers. Embodiments of the invention can also include, but are not limited to, bone implants with dynamically expanding tips, bone implants with expanding rings along the axis of the implant, and/or other attachable accessories or coatings that modify other bone implants in order to add such dynamic expansion behavior as described herein. Embodiments of the invention can also include devices having dynamically expandable structures on the side and lateral portions of devices including fixation devices, implants and bone anchors, such as dynamically expandable portions provided in the form of fingers, feet, and studs, that reduce unwanted penetration, migration, stress shielding, and other effects deleterious to bone health and implant stability due to side, lateral or oblique loading to the device.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

SUMMARY OF THE INVENTION

The present invention may involve several broad forms. Embodiments of the present invention may include one or any combination of the different broad forms herein described.

In a first aspect, the current invention provides an implant for securing into bone, the implant comprising:
 a shaft for penetration of bone tissue having a distal end and a proximal end, where force is applied to the proximal end to move the distal end into the bone tissue; and
 a dynamically expanding tip operably connected to the shaft, where the dynamically expanding tip expands laterally from the shaft when a force is applied to the distal end of the implant.

Preferably, the dynamically expanding tip comprises an elastomeric material. Alternatively, the dynamically expanding tip comprises a dynamically expanding mechanism.

The dynamically expanding tip is preferably an end piece operably connected to the distal end of the shaft.

In an embodiment, the dynamically expanding tip may be a ring that circumscribes the shaft.

In an embodiment, the implant further comprising at least one articulating wall at the distal end of the shaft and wherein the dynamically expanding tip is an insert disposed into the distal end of the shaft, where the at least one or more articulating wall is movable by the lateral expansion of the insert.

The implant may include a thread portion extending about the shaft for engagement with the bone tissue, and wherein the implant is a screw device.

In a second aspect, the current invention provides a system for engagement with a bone of a patient, the system comprising:
 a shaft portion for penetration of bone tissue having a distal end and a proximal end, where force is applied to the proximal end to move the distal end into the bone tissue; and
  a deformable element portion operably adjacent the distal end of the shaft portion, the deformable element portion being sized and formed from a material such that upon adjacent bone tissue to the deformable element portion being urged against the deformable element portion in a direction of at least from the distal end towards the proximal end of the shaft portion, the deformable element portion deforms in at least a lateral direction with respect to the longitudinal axis of the shaft portion;
  wherein deformation of the deformable element portion causes an increased contact area between the deformable element portion and the adjacent bone tissue and a reduction in stress in the adjacent bone tissue.

The reduction in stress in the adjacent bone tissue reduces deformation of the adjacent bone tissue so as to resist penetration of the deformable element portion into the adjacent bone tissue.

The deformable element portion may be affixed adjacent to the distal end of the shaft prior portion to penetration of bone tissue.

The deformable element portion may be provided as a separate element from the shaft portion, so as to allow delivery of the deformable element portion into an aperture in bone material prior to penetration of the shaft portion.

In an embodiment, the deformable element portion may be provided as a settable material, so as to allow the deformable element portion to be delivered into an aperture in bone material in a non-formed state, prior to penetration of the shaft portion.

In an embodiment, the deformable element portion and the shaft portion maybe unitary formed, and the deformable element portion and the shaft portion may be formed from a same material.

The deformable element portion may be formed from an elastomeric material. Alternatively, the deformable element portion may be formed from a rubberized material.

In an embodiment, the deformable element portion may be formed from Polydimethylsiloxane (PDMS).

Preferably, the deformable element portion is formed from an elastically deformable material such that upon a reduction in force urging adjacent bone tissue to the deformable element portion being urged against the deformable element portion, the elasticity of the deformable element portion urges the deformable element portion towards its non-deformed state.

The deformable element portion is preferably formed from an expandable material.

The deformable element portion is preferably formed from a material such that upon deformation of the deformable element portion the deformable element portion is deformed and extends into pores and cavities present in adjacent bone tissue so as to further increase the contact area between the deformable element portion and the adjacent bone tissue.

Preferably, the deformable element portion is formed from a material such that upon deformation of the deformable element portion an increase frictional force is formed between the deformable element portion and adjacent bone tissue so as to resist penetration of the deformable element portion into the adjacent bone tissue.

In a third aspect, the current invention provides a device for engagement with a bone of a patient, the device comprising:
 a body portion for penetration of and fixation to bone tissue, the body portion having a distal end and a proximal end; and
 a deformable element portion extending along at least a portion of the body portion in a direction of from the distal end towards the proximal end of the body portion,
 wherein the deformable element portion is sized and formed from a material such that upon adjacent bone tissue to the deformable element portion being urged against the deformable element portion in a direction of at least normal to the direction of from the distal end towards the proximal end of the body portion, the deformable element portion deforms in at least a direction of from the distal end towards the proximal end of the body portion wherein deformation of the deformable element portion causes an increased contact area between the deformable element portion and the adjacent bone tissue and a reduction in stress in the adjacent bone tissue.

Preferably, the reduction in stress in the adjacent bone tissue reduces deformation of the adjacent bone tissue so as to oppose migration of the deformable element portion and the device into the adjacent bone tissue.

The deformable element portion may be disposed within the body portion and is deployable so as to extend in the direction of at least normal to the direction of from the distal end towards the proximal end of the body portion upon the device being engaged within the bone tissue.

The body portion preferably includes a passage therein extending in a direction of from the proximal end towards the distal end of the body portion and a plurality of apertures providing communication from said passage to external of the body portion, wherein the deformable element portion is deployable from within the passage of the body portion so as to extend in the direction of at least normal from the direction of from the proximal end towards the distal end of the body portion.

The deformable element portion may be deployable by way of being urged through said apertures by urging a deployment into the passage of the body portion from the proximal end of the body portion.

The body portion may include a thread portion extending about an axis of the body portion of from the proximal end towards the distal end for engagement with the bone tissue.

In an embodiment, the deformable element portion may be a separate element from the body portion, so as to allow delivery of the deformable element portion into an aperture in bone material prior to the device being engaged with bone tissue.

The deformable element portion may be provided as a settable material, so as to allow the deformable element portion to be delivered into an aperture in bone material in a non-formed state, prior to the device being engaged with bone tissue. Preferably, the body portion includes a passage therein extending in a direction of from the proximal end towards the distal end of the body portion and a plurality of apertures providing communication from said passage to external of the body portion, wherein the deformable element portion is provided as a settable material is deployable from within the passage of the body portion so as to extend in the direction of at least normal from the direction of from the proximal end towards the distal end of the body portion, and wherein the settable material in introduced into said passage from the proximal end of the body portion.

The body portion may include a thread portion extending about an axis of the body portion of from the proximal end towards the distal end for engagement with the bone tissue.

The deformable element portion and the body portion may be unitary formed.

The deformable element portion may be formed from an elastomeric material. Alternatively, the deformable element portion may be formed from a rubberized material.

In an embodiment, the deformable element portion may be formed from Polydimethylsiloxane (PDMS).

Preferably, the deformable element portion is formed from an elastically deformable material such that upon a reduction in force urging adjacent bone tissue to the deformable element portion being urged against the deformable element portion, the elasticity of the deformable element portion urges the deformable element portion towards its non-deformed state.

The deformable element portion may be formed from an expandable material.

Preferably, the deformable element portion is formed from a material such that upon deformation of the deformable element portion the deformable element portion is deformed and extends into pores and cavities present in adjacent bone tissue so as to further increase the contact area between the deformable element portion and the adjacent bone tissue.

The deformable element portion may be formed from a material such that upon deformation of the deformable element portion an increase frictional force is formed between the deformable element portion and adjacent bone tissue so as to resist penetration of the deformable element portion into the adjacent bone tissue.

In an embodiment, a further deformable element portion adjacent the distal end of the body portion may be included, the deformable element portion being sized and formed from a material such that upon adjacent bone tissue to the deformable element portion being urged against the deformable element portion in a direction of at least from the distal end towards the proximal end of the body portion, the deformable element portion deforms in at least a normal direction with respect to the direction of from the distal end towards the proximal end of the body portion, longitudinal axis of the shaft portion, and wherein deformation of the deformable element portion causes an increased contact area between the deformable element portion and the adjacent bone tissue and a reduction in stress in the adjacent bone tissue.

In an embodiment, the device is a screw type fixation device.

In another embodiment, the device is a pedicle screw.

In a further embodiment, the device is a suture anchor.

In a fourth aspect, the current invention provides a system for providing control of movement of a first bone portion relative to a second bone portion, the system comprising:

two or more devices according to the third aspect, whereby at least one first device being for engagement with the first bone portion and at least one second device being for engagement with the second bone portion; and one or more support devices, wherein the support device is engageable with a proximal end portion of a first device and is engageable with a proximal end portion of a second device;

wherein upon engagement of the first device with the first bone portion, upon engagement of the second device with the second bone portion and upon engagement of the support device with the proximal end portion of the first device and with the proximal end portion of the second device, control of movement is provided between the first bone portion and the second bone portion.

Preferably, the support device provides controlled movement of the first bone portion relative to the second bone portion.

Alternatively, the support device provides restriction of movement of the first bone portion relative to the second bone portion.

In an embodiment the support device is elastically deformable.

In an embodiment, the support device provides controlled fixation of the first bone portion relative to the second bone portion.

In another embodiment, the support device provides fixation of the first bone portion relative to the second bone portion.

In a fifth aspect, the current invention provides a device for engagement with a bone of a patient, the device comprising:

a body portion for penetration of and fixation to bone tissue, the body portion having a distal end and a proximal end; and a deformable element portion extending from the body portion, wherein the deformable element portion is sized and formed from a material such that upon adjacent bone tissue to the deformable element portion being urged against the deformable element portion, the deformable element portion deforms in at least a direction of at least laterally in relation to the direction from which the adjacent bone tissue is urged against the deformable element; and wherein deformation of the deformable element portion causes an increased contact area between the deformable element portion and the adjacent bone tissue and a reduction in stress in the adjacent bone tissue and opposes migration of the body portion into the adjacent bone tissue.

In a sixth aspect, the current invention provides a deformable element for opposing migration of a bone engagement device within bone tissue, the deformable element comprising:

wherein the deformable element is sized and formed from a material such that upon being disposed between bone tissue and a bone fixation device and upon adjacent bone tissue to the deformable element being urged against the deformable element, the deformable element deforms in at least a direction of at least laterally in relation to the direction from which the adjacent bone tissue is urged against the deformable element; and wherein deformation of the deformable element causes an increased contact area between the deformable element and the adjacent bone tissue and a reduction in stress in the adjacent bone tissue and opposes migration of the bone fixation device into the adjacent bone tissue.

The deformable element may include an engagement surface for engagement with bone tissue and an abutment surface for abutment to a bone fixation device.

The deformable element may include a bearing portion upon which the abutment surface is provided against which bone engagement device abuts upon which the bone engagement device is urged, the bearing portion being formed from a material so as to resist penetration of the bone engagement device into the deformable element.

In a seventh aspect, the current invention provides a kit comprising one of deformable elements according to the sixth aspect, and one or more bone engagement devices.

In an eighth aspect, the current invention provides a method of reducing migration of a bone engagement device within bone tissue; said method including the steps of:

(i) providing a bone engagement device having the device comprising: a body portion for penetration of and fixation to bone tissue, the body portion having a distal end and a proximal end; and a deformable element portion extending from the body portion; and (ii) inserting the bone engagement device within bone tissue of a subject;

wherein the deformable element portion is sized and formed from a material such that upon adjacent bone tissue to the deformable element portion being urged against the deformable element portion, the deformable element portion deforms in at least a direction of at least laterally in relation to the direction from which the adjacent bone tissue is urged against the deformable element; and wherein deformation of the deformable element portion causes an increased contact area between the deformable element portion and the adjacent bone tissue and a reduction in stress in the adjacent bone tissue and opposes migration of the body portion into the adjacent bone tissue.

In a ninth aspect, the current invention provides a method of reducing migration of a bone engagement device within bone tissue; said method including the steps of:

(i) providing a deformable element;

(ii) deploying the deformable element within an aperture within bone tissue of a subject (iii) inserting a bone engagement device within said aperture and urging said bone engagement device in a distal direction to as to abut against the deformable element and such that the deformable element is abutted against adjacent bone tissue;

wherein the deformable element is sized and formed from a material such that upon the deformable element being urged against the deformable element, the deformable element deforms in at least a direction of at least laterally in relation to the direction from which the adjacent bone tissue is urged against the deformable element; and wherein deformation of the deformable element causes an increased contact area between the deformable element and the adjacent bone tissue and a reduction in stress in the adjacent bone tissue and opposes migration of the bone fixation device into the adjacent bone tissue.

BRIEF DESCRIPTION OF THE DRAWINGS

In order that a more precise understanding of the above-recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIGS. 3A-3H illustrate methods and techniques by which a dynamically expandable tip can be attached to the distal end of a bone implant such as a bone screw.

FIGS. 4A-4H illustrate further methods and techniques by which a dynamically expandable tip can be attached to the proximal end of a bone implant such as a bone screw.

FIGS. 5A-5C illustrate embodiments of bone screws, according to the subject invention, for fixation of fractures, which have a dynamically expandable ring located either in a relatively medial FIG. 5A, or relatively proximal FIG. 5B position on the bone screw. Additionally, rings of elastic material may be placed between screw threads FIG. 5C.

FIGS. 6A and 6B illustrate another embodiment of a bone screw, according to the subject invention, for fixation of fractures with a dynamically expandable threaded insert, presented both before FIG. 6A, and during FIG. 6B axial compression via the rotation of the distal end of the implant.

FIGS. 7A and 7B illustrate embodiments of a bone screw, according to the subject invention, for fixation of fractures with a dynamically expandable insert, presented both before FIG. 7A, and during FIG. 7B axial compression.

FIGS. 8A and 8B illustrate embodiments of attachable dynamically expandable tip accessories that, according to the subject invention, can be screwed into FIG. 8A or slid over FIG. 8B the distal or proximal ends of currently known bone implants.

FIGS. 8C(i)-(v) illustrate an embodiment of a bone screw according to the subject in invention having a dynamically expandable tip insertable separately into a cavity in bone tissue prior to insertion of the bone screw body.

FIGS. 13A through 13H illustrate different embodiments of the subject invention utilized for repair of different types of bone fractures, where FIG. 13A demonstrates fixation implants for repair of lower distal extremity fractures, FIG. 13B demonstrates fixation implants for repair of hip fractures, FIG. 13C demonstrates fixation implants for repair of shoulder fractures, FIG. 13D demonstrates fixation implants for repair of cranial fractures, FIG. 13E demonstrates a dental implant for replacement or repair of teeth, FIG. 13F demonstrates spinal implants for treatment or fixation of vertebral fractures, FIG. 13G demonstrates a spinal implant for relieving pressure at the site of a vertebral compression fracture, and FIG. 13H demonstrates fixation implants for repair of upper distal extremity fractures.

FIGS. 15A and 15B represent the results of two pilot studies conducted to compare the effectiveness of a typical blunt-tip stainless steel bone screw at preventing cut-out, with a prototype bone screw, according to the subject invention, having a dynamically expandable elastomeric polymer tip after implantation in FIG. 15A porcine bone tissue, and in FIG. 15B artificial bone tissue made of polyurethane foam.

FIGS. 16A and 16B illustrate another embodiment where the dynamically expanding tip is an insert placed within the distal tip of an implant FIG. 16A and is adjustable with a plug that can be moved within a duct in the implant FIG. 16B.

FIGS. 17A and 17B illustrate an embodiment of a bone screw as it is inserted into a pilot hole in a fractured bone and over which a bone plate has been placed.

FIGS. 17C (i)-(iii) illustrate one example of the process of attaching the bone screw to the bone plate FIG. 17C(i), loading the bone such that a distal region of bone tissue compresses the tip of the bone screw FIG. 17C(ii), and removing the load such that the distal tip returns to its original (relaxed) state FIG. 17C(iii).

FIGS. 21A(i)-21A(iii) illustrate an embodiment of a bone screw that is made completely of an expandable material such as an elastic polymer, during the process of attaching the bone screw to the bone plate FIG. 21A, loading the bone such that a distal region of bone tissue compresses the tip of the bone screw FIG. 21B, and removing the load such that the distal tip returns to its original (relaxed) state FIG. 21C.

FIGS. 22A-22C illustrate how the expanding tip of a bone screw embodiment of the current invention FIG. 22B, when undergoing compression by cancellous bone tissue FIG. 22C can expand to fill the pores and cavities of said tissue FIG. 22A.

FIGS. 26A and 26B illustrate an embodiment of bone screw according to the current invention depicting the deployment of dynamically expandable side or lateral portion(s), distal tip, and core, from an un-deployed configuration of FIG. 26A to a deployed configuration of FIG. 26B.

FIGS. 27A and 27B illustrate another embodiment of bone screw according to the current invention depicting the deployment of dynamically expandable side or lateral portion(s), distal tip, and core, from an un-deployed configuration of FIG. 27A to a deployed configuration of FIG. 27B.

28A illustrates the bone screw embodiment following implantation in a vertebra through the pedicle of the vertebrae with dynamically expandable portions in an un-deployed configuration, and FIG. 28B depicts the dynamically expandable portions in an deployed configuration.

FIG. 29A illustrates the bone screw embodiment following implantation in a vertebra through the pedicle of the vertebrae with dynamically expandable portions in an un-deployed configuration, and FIG. 29B depicts the dynamically expandable portions in an deployed configuration.

FIGS. 32A, 32B and 32C illustrate how the dynamically expandable side or lateral portion(s) of an embodiment of a bone screw of the current invention undergoes expansion from compression by cancellous or trabecular bone tissue whereby FIG. 22C depicts the dynamically expandable side or lateral portion(s) expanding to fill the pores and cavities of said tissue.

FIG. 39 shows an embodiment of a bone screw embodiment of the current invention having a dynamically expandable side or lateral portion(s) consisting of a mechanism designed to approximate the mechanical behavior of an elastomeric material such as a rubber or elastic foam.

FIGS. 40A, 40B and 40C depict an embodiment of a device of the current invention used as a suture anchor for repair of connective tissue, muscle, and/or other soft tissue, and for connection of such tissue to bone.

FIGS. 41($i$)-41($iv$) depict an embodiment of a deformable element according to the current invention, whereby the deformable element is provided as a separate element from a bone engagement device and is deployable within an aperture with bone tissue of a subject prior to deployment of a bone fixation device.

FIGS. 42($i$)-42($iv$) depict a further embodiment of a deformable element according to the current invention, whereby the deformable element is provided as a separate element from a bone engagement device and is deployable within an aperture with bone tissue of a subject prior to deployment of a bone fixation device.

DETAILED DESCRIPTION OF THE DRAWINGS

Figures 1A, 1B, 1C:
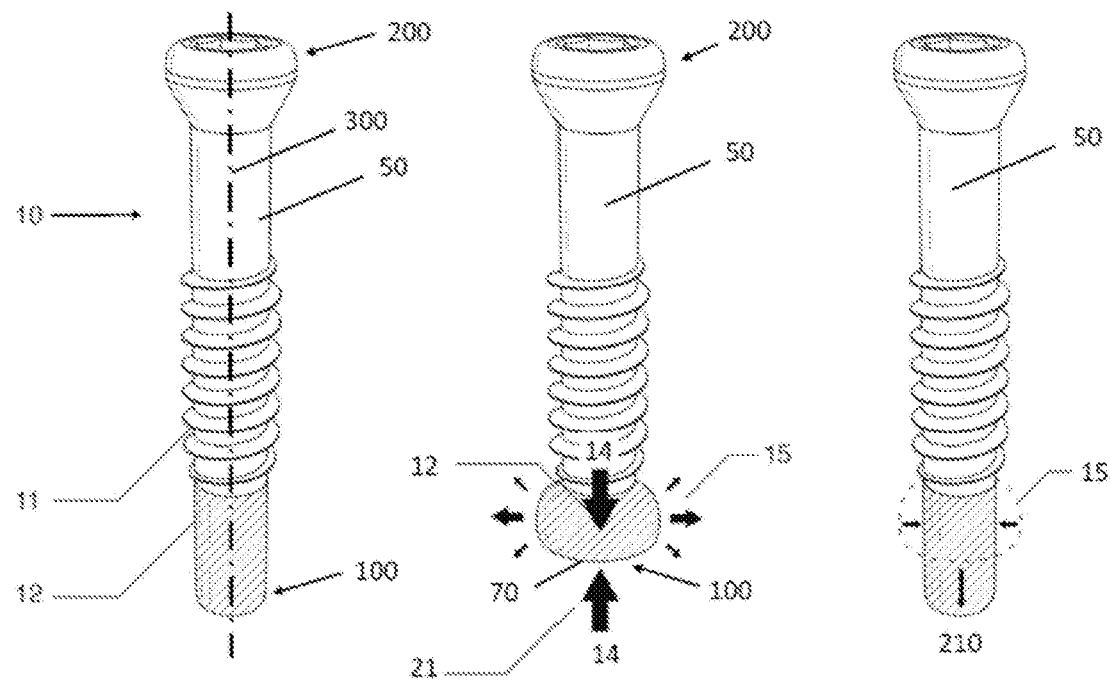
FIGS. 1A, 1B, and 1C illustrate an embodiment of a bone screw, according to the subject invention, for fixation of fractures with a dynamically expandable distal tip, before FIG. 1A, during FIG. 1B, and after FIG. 1C axial compression of the screw.

The subject invention pertains to embodiments of bone implantation systems and devices. Embodiments of the subject invention provide a system for engagement with a bone of a patient, which can have a shaft portion for penetration of bone tissue, the shaft portion having a distal end and a proximal end, where force is applied to the proximal end to move the distal end into the bone tissue.

The system can further include a deformable element portion operably adjacent the distal end of the shaft portion, the deformable element portion being sized and formed from a material such that upon adjacent bone tissue to the deformable element portion being urged against the deformable element portion in a direction of at least from the distal end towards the proximal end of the shaft portion, the deformable element portion deforms in at least a lateral direction with respect to the longitudinal axis of the shaft portion. Deformation of the deformable element portion causes an increased contact area between the deformable element portion and the adjacent bone tissue and a reduction in stress in the adjacent bone tissue. The reduction in stress in the adjacent bone tissue reduces deformation of the adjacent bone tissue so as to resist penetration of the deformable element portion into the adjacent bone tissue.

The deformable element portion may also be configured with a fixation device such that it is deployable after insertion into a bony body, facilitating insertion by allowing the deformable element portion to be retained within the shaft portion while, for example, a bone screw as an embodiment of the current invention which is screwed into a bony body without abrading or damaging the deformable element portion against the bone tissue.

Such a device s may include a deformable element portion on the side of the shaft portion of the device, or that is lateral to the shaft portion. Deformation of the side or lateral deformable element portion causes an increased contact area between the side or lateral deformable element portion and the adjacent bone tissue and a reduction in stress in the adjacent bone tissue. The reduction in stress in the adjacent bone tissue reduces deformation of the adjacent bone tissue so as to resist penetration of the side or lateral deformable element portion into the adjacent bone tissue.

More specifically, the subject invention provides one or more embodiment(s) of bone implant screws or similar devices capable of being secured within bone tissue and that inhibit undesirable movement of the bone implant screw after implantation. In particular, the bone implant screw embodiments of the subject invention inhibit the "cut-out" or bone penetration phenomenon, as well, or alternatively, as aseptic loosening, migration, and/or stress shielding, often experienced with other known devices.

The following description will disclose that the subject invention is particularly useful in the field of orthopedic surgical procedures, in particular devices used for the treatment and/or repair of bone fractures. However, a person with skill in the art will be able to recognize numerous other uses that would be applicable to the devices and methods of the subject invention. While the subject application describes, and many of the terms herein relate to, a use for treatment and/or repair of bone tissue, modifications for other uses, apparent to a person with skill in the art and having benefit of the subject disclosure, are contemplated to be within the scope of the present invention.

In other surgical disciplines whereby soft tissue or connective tissue is required to be secured relative to bone or relative to other soft tissue or connective tissue, the current invention may provide an anchor type device affixable to bone tissue and the device may have a portion to which a suture material may be engaged therewith, such that the suture may be engaged with soft tissue or connective tissue and the device provides an anchor point for the soft tissue or connective tissue relative to the bone.

Reference is made throughout the application to the "proximal end" and "distal end" of a bone screw. As used herein, the proximal end is that end to which pressure and/or torque can be applied to drive a bone screw into bone tissue. Conversely, the distal end is that end that moves deeper into and through interior bone tissue.

Reference is made throughout the application to the "side" and "lateral" portion of a bone screw. As used herein, the side or lateral portion is that portion to which pressure or loading may be applied by physiological loading of the bone in a direction approximately perpendicular to the long axis of the bone screw. Such pressure may arise, for instance, as a result of bone tissue being urged against the shaft of the bone screw, or vice versa. Those skilled in the art will understand that such side or lateral loading may also include a component of load which is not perpendicular to the long axis of the screw.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components.

With reference to the attached figures, which show certain embodiments of the subject invention, it can be seen that FIGS. 1A, 1B, and 1C illustrate one embodiment of an implant 10, according to the subject invention, such as, by way of non-limiting example, having a shaft portion as a bone screw, that can be used for internal fixation of fractures and having a deformable element portion as a dynamically expandable tip. FIG. 1A illustrates an embodiment of, a bone screw type implant 10 that includes one or more threaded areas 11 along at least a portion of the longitudinal length 300 of the shaft 50, and internal or external features, such as shown, for example, in FIGS. 3A-3H and 4A-4H, that permit the attachment of a dynamically expandable tip 12.

In one embodiment, a dynamically expandable tip 12 is a deformable structure that includes one or more elastomeric polymers having a Poisson Ratio of from 0.3 to 0.5 and a Young's Modulus of from 0.001 GPa to 0.5 GPa. Such elastomeric polymers can include, but are not limited to, saturated and unsaturated natural and artificial rubbers and foams such as polyisoprene, fluorinated polymers, brominated polymers, chloroprenes, butyl rubbers, styrene-butadiene rubbers, nitrile rubbers, ethylene-propylene rubbers, epichlorohydrin rubbers, silicone, silicone rubbers, polydimethylsiloxane, fluorosilicone rubbers, fluoroelastomer rubbers, perfluoroelastomer rubbers, polyvinyl alcohol, polyvinyl acetate, polyvinyl chloride, polycaprolactone, polylactic acide, ethyl-vinyl acetate, latex rubbers, collagens, thermoplastic elastomers, proteins such as resilin and elastin, elastolefin and polysulfide rubbers. In a specific embodiment, a dynamically expanding tip 12 is formed from a Polydimethylsiloxane (PDMS), a type of silicone rubber suitable for implantation into a body.

Figure 11A:
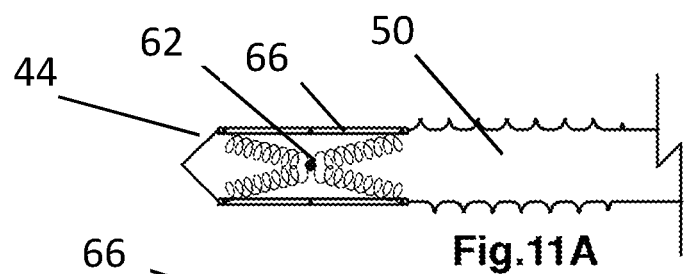
FIGS. 11A and 11B illustrate another embodiment of an implant, according to the subject invention, with a hollow tip that allows a dynamically expandable mechanism to be inserted, as shown both before FIG. 11A and during FIG. 11B compression.
Figure 11B:
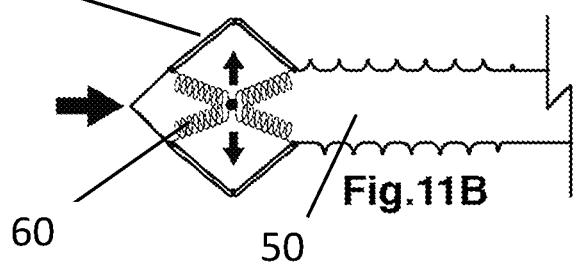

A dynamically expanding tip 12 can also employ one or more dynamically expanding mechanisms 60, such as, for example, those including a system of springs or cams, as shown in FIGS. 11A and 11B that are mechanically configured to approximate the behavior of elastomeric polymers. These dynamically expanding mechanisms can be fabricated from relatively rigid materials, including, but not limited to, metal alloys, such as steel, titanium and aluminum alloys, ceramics, or rigid polymers, or a combination of such rigid materials with flexible or elastic materials, such as elastomeric polymers, spring steels, nylon, and nitinol. Composites that include one or more elastomeric materials and/or one or more rigid materials can also be employed to mimic the properties of materials having a Poisson Ratio of from 0.3 to 0.5 and Young's Modulus of from 0.001 GPa to 0.5 GPa.

The dimensions of an implant 10 can depend upon the type of material being utilized for the shaft or other rigid parts of the implant, the intended location in the body, the maximum applicable load to be applied to the implant, the type of material utilized for the dynamically expanding tip, and other factors that would be understood by a person with skill in the art. In a particular embodiment of a locking screw, the length of the rigid shaft or screw portion of the implant, between the distal end 100 and the proximal end 200, is between approximately 30 mm and approximately 100 mm and the diameter is between approximately 2.5 mm and approximately 6 mm. In a more specific embodiment, the length of the rigid shaft or screw portion of the implant is between approximately 40 mm and approximately 90 mm and the diameter is between approximately 3.5 mm and approximately 5 mm.

In a particular embodiment of a locking screw, the exposed length of the dynamically expanding tip, that is, the length exposed between the distal end 100 and the proximal end 200 and does not include any portion that may be within the distal end of the rigid part of the implant, is between approximately 7 mm and approximately 13 mm. In a more particular embodiment, the exposed length of a dynamically expanding tip is between approximately 8 mm and approximately 12 mm. In a specific embodiment, the exposed length of a dynamically expanding tip is approximately 10 mm.

The diameter of the exposed length of a dynamically expanding tip can be greater than or less than the diameter of the distal end 100 of the rigid portion of the implant. Ideally, the dynamically expanding tip is at least the same or approximately the same diameter as the distal end of the rigid portion of the implant. The diameter can also be inconsistent where one part of the dynamically expanding tip can have a larger or smaller diameter than another part of the dynamically expanding tip. For example, the proximal end of a dynamically expanding tip can have a smaller diameter than the distal end. In one particular embodiment of a locking screw, the diameter of the exposed length of a dynamically expanding tip is between approximately 2 mm and approximately 4.5 mm. In a more particular embodiment, the diameter of the exposed length of a dynamically expanding tip is between approximately 2.5 mm and 4 mm.

FIG. 1B shows an embodiment of a bone screw implant 10 with a dynamically expanding tip 12 being deformed in shape as axial compression force 14 is translated into lateral expansion force 15, due to the material properties (e.g., Poisson's Ratio and Young's Modulus) or mechanical configuration (e.g., a spring-loaded mechanism, such as depicted in FIGS. 11A and 11B) of the distally, or approximately distally, located 100 dynamically expanding tip 12. In accordance with the subject invention, deformation of the tip 12 increases the contact area 70 between the tip 12 and adjacent bone tissue, which reduces localized contact stress between the tip 12 and the bone. The reduction of stress in bone adjacent the deformable element, which is being urged against the deformable element as provided by the embodiments of subject invention, inhibits the above-mentioned "cut-out" by such stress reduction. As an additional effect, when an implant 10 embodiment of the subject invention has been placed in bone, the lateral expansion force 15 of the dynamically expanding tip 12 can increase the kinetic force of friction with the bone tissue. This can occur because during compressive force 21, there is formed at least one enlarged contact surface 70 on the dynamically expanding tip 12 that presses against the bone tissue and can resist an axial compressive force 14 applied by the bone tissue as seen in FIG. 1B. This contact surface, which provides increased frictional force 17, can resist further penetration of an implant, such as a bone screw embodiment, past the point of the implant location, while allowing for small magnitude movements of the bone with minimal damage to the bone tissue.

FIG. 1C shows the dynamically expandable tip restored to the original, or almost the original, un-deformed shape after cessation of the axial compression force 14. After cessation as shown, in the event screw removal is required, this can be beneficial in withdrawal of the screw from bone.

Figures 2A, 2B:
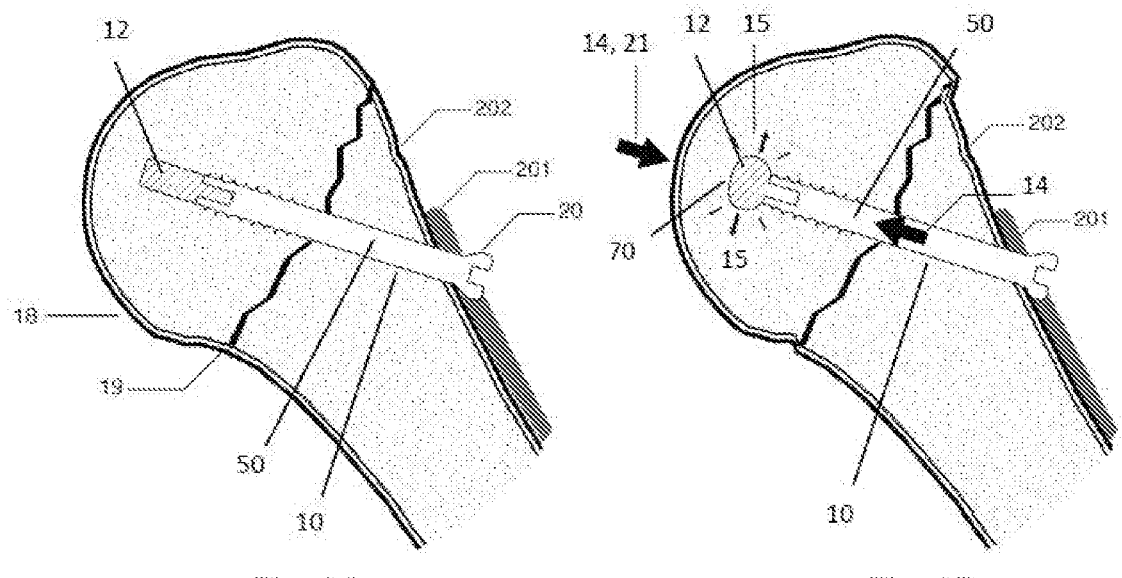
FIGS. 2A and 2B illustrate an embodiment of a fixation device, according to the subject invention, for a neck fracture of the proximal humerus, both before FIG. 2A and during FIG. 2B axial compression of the screw after implantation in the bone.

In FIG. 2A, there is shown an implant 10 embodiment, such as the bone screw shown in FIGS. 1A-1C, implanted into a long bone, such as a humerus 18, with a fracture along the anatomical or surgical neck 19. With this embodiment, one or more bone screw implants can be implanted in the bone. Alternatively, one or more bone screw implants can be used in combination with other devices and/or other types of fixation implants such as, but not limited to, other implant screws, plates, rods, wires, and combinations of these and other devices.

The implant embodiments of the subject invention can be implanted with or without a pre-drilled pilot hole to aid in bone insertion. FIG. 2B shows an embodiment of a bone screw implant 10 translating a compressive force 21 into deformation of the tip 12, thereby increasing contact area between implant and bone tissue and resisting further penetration of the bone screw into the bone tissue. The increased surface area of the contact surface can also support the bone tissue and inhibit the collapse of the bone. As an additional effect, a bone screw implant 10 can translate a compressive force 21 into lateral expansion force 15, increasing frictional force between the tip and bone tissue 17 and further resist penetration of the bone screw into the bone tissue. A bone plate, 201, may form a secure connection between the proximal end of the screw 200 and the bone head or shaft 202, such that compressive force applied to the bone head or shaft translates to the bone screw. Whilst not depicted in the drawings, those skilled in the art will readily appreciate that the screw 10 is fixedly engaged with the bone plate 201 such that no relative motion exists therebetween. In FIGS. 3A-3H, various non-limiting methods and techniques are shown for attaching an embodiment of a dynamically expanding tip 12 formed as an end piece 20 of elastic or deformable material to the distal end of an implant, such as, for example, a bone screw similar to the embodiment of a bone screw with dynamically expanding tip depicted in FIG. 1. These method and techniques can include, but are not limited to:

attaching a smooth boss tip 23 formed at the proximal end 200 of the dynamically expanding tip 12 into a receiving cavity 51 in the distal end of an implant, as shown, for example, in FIG. 3A;

screwing a threaded boss tip 24 formed at the proximal end 200 of the dynamically expanding tip 12 into a tapped cavity 52 in the distal end 100 of an implant, as shown, for example, in FIG. 3B;

attaching a dynamically expanding tip 12 having a concavity 25 on the proximal end 200 onto the distal end of an implant having a compatibly configured convex feature 53 on the distal end 100, such as, by way of non-limiting example, a mechanical hook, detents, ratchet teeth, or similar type of structure that can operably connect with the concavity, such as shown, for example, in FIG. 3C;

screwing a dynamically expanding tip 12 with a threaded or tapped tip 26 in the proximal end 200 onto a threaded boss 54 extending from the distal end 100 of an implant, as shown, for example, in FIG. 3D;

attaching a dynamically expanding tip 12 having an indented tip 27 with one or more indentations, into a deformable cavity 55 in the distal end 100 of an implant, where, in one embodiment, the distal end of the implant has one or more crimping sections 56 that can be crushed or otherwise deformed over and/or around the indented tip to hold it in place within the deformable cavity, as shown, for example, in FIG. 3E.

In other embodiments, the dynamically expanding tip 12 comprises a material that can exist, at least for a short period of time, in a liquid or semi-liquid form, so that it can be directly molded onto and/or into one or more structures at the distal end 100 of an implant. The material can then harden, solidify, congeal, set, stiffen, or otherwise change form so that the material remains attached to the implant and is inhibited from separating from the implant. By way of non-limiting example, a liquid or semi-liquid material, which can form a dynamically expanding tip, can be introduced into at or about the distal end of an implant having one or more of:

one or more channels 28, which can be of various shapes and/or sizes, into which the material of a dynamically expanding tip can migrate and fill, such as shown, for example, in FIG. 3F; and one or more transverse cavities 29, which can be of various shapes and/or sizes, into which the material of a dynamically expanding tip can migrate and fill, such as shown, for example in FIG. 3G.

In another embodiment, a dynamically expanding tip 12 can be secured with one or more pins 30. Pins can be used with a dynamically expanding tip 12, such as those shown in FIGS. 3A-3E. Pins can also be used with dynamically expanding tip 12 formed into the implant, such as those shown in FIGS. 3F-3H. In one embodiment, the distal end of an implant has one or more through holes 57 that communicate one side of the tip to another side of the tip, whereby one or more pins 30 can traverse the through holes thereby securing, or further securing, a dynamically expanding tip 12 onto the distal end of an implant, such as shown, for example, in FIG. 3H. In the particular example, shown in FIG. 3H, a smooth boss tip 23 on dynamically expanding tip is inserted into a receiving cavity 51 at the distal end of an implant. Through holes 30 can go through both the tip and the receiving cavity and pin placed therein to aid in securing the tip in the receiving cavity.

In FIG. 4, there is shown various alternative methods and techniques for attaching the dynamically expanding tip in the form of an end piece 20 to the proximal end 200 of an implant, such as, for example, a bone screw similar to the type depicted in FIG. 1. These methods and techniques can include, but are not limited to:

attaching a smooth boss 23 extending from the dynamically expanding tip 12 into a receiving cavity 51 in the proximal end 100 of the implant, as shown, for example in FIG. 4A;

screwing a threaded boss 24, extending from the dynamically expanding tip 12, into a tapped cavity 52 in the proximal end of the implant, as shown, for example in FIG. 4B;

attaching the dynamically expanding tip 12, having a concavity 26, to a convex feature 53 on the proximal end of the implant, such as, by way of non-limiting example, a mechanical hook, detents, ratchet teeth, or similar type of structure that can operably connect with the concavity, such as shown, for example, in FIG. 4C;

screwing a dynamically expanding tip 12 onto a threaded boss 54 extending from the proximal end of the implant such as shown, for example, in FIG. 4D;

attaching a dynamically expanding tip 12 having an indented tip 27 with one or more indentations into a deformable cavity 55 in the proximal end 200 of an implant, where, in one embodiment the distal end of the implant has one or more crimping sections 56 that can be crushed or otherwise deformed over and/or around the indented tip to hold it in place within the deformable cavity, as shown, for example, in FIG. 4E.

A dynamically expanding tip 12 in the form of an end piece 20 can also be fixedly attached to the proximal end 200 of an implant by utilizing a material for the tip 12 that can exist, at least for a short period of time, in a liquid or semi-liquid form, so that it can be directly molded onto and/or into one or more structures at the distal end 100 of an implant. These methods and techniques have been described above and are reiterated here and illustrated in FIGS. 4F-4H with regard to attaching a dynamically expanding tip to the proximal end 200 of an implant.

Other methods and techniques can be employed in addition to the ones discussed above and combinations of these techniques can also be used. A person with skill in the art would be able to determine which of these, or other methods and techniques, would be best suited for attaching an end piece 20 embodiment of a dynamically expanding tip 12, according to the subject invention, by considering the type of implant, material of the dynamically expanding tip, and other factors. Such variations which provide the same function, in substantially the same way, with substantially the same result are within the scope of this invention.

In an alternative embodiment, a dynamically expanding tip 12 can be formed or placed so that it circumscribes or partially circumscribes the body or shaft 50 of the implant. In other words, an implant 10 can have a dynamically expanding insert between the distal end 100 and the proximal end 200. In a particular embodiment, a dynamically expanding tip 12 is configured as a dynamically expanding ring 40 that encircles, or at least partially encircles, the exterior surface 150 of an implant 10. With this embodiment, a dynamically expanding ring 40 can be positioned at almost any location on an implant 10 as long as the implant is configured to ensure that the dynamically expanding ring 40 is secured in place.

In FIGS. 5A and 5B there is shown embodiments in which an implant includes a dynamically expandable ring 40 and which can function similarly to the dynamically expandable tip 12 described above and shown in FIGS. 1-4H. In one embodiment, shown, by way of example, in FIG. 5A, a dynamically expandable ring 40 is positioned at or about the medial position along the longitudinal length 300 of the implant 10, where it can be compressed by an annular shoulder 61, when a forward or distal directed 100 penetrative movement is applied to the implant. In FIG. 5B, there is shown an embodiment of a similar dynamically expandable ring 40 positioned nearer to, or at, the proximal end of the implant, such that an annular shoulder at or about the proximal end 200 of the implant can be compressed against the expandable ring 40, when a forward or distal directed 100 penetrative movement is applied to the implant. As illustrated in FIG. 5C, rings of elastic or deformable material 203, may be located between the screw threads.

In another embodiment, shown in FIGS. 6A and 6B, an implant includes a dynamically expandable ring 40 with internal threads 41, located at a point along the longitudinal length 300 of an implant, for example, in the medial position of the implant. In FIG. 6A, this embodiment is shown in a relaxed state, prior to compression of the expandable ring 40. In FIG. 6B, this embodiment is shown during or after compression of the threaded expandable ring 40, through rotation of the distal end of the implant, through and into bone tissue. For example, screwing the implant through bone tissue can cause the expandable ring to be compressed between the bone tissue and the annular shoulder, causing the lateral expansion 15 discussed above.

In yet another embodiment, shown by way of example, in FIGS. 7A and 7B an implant includes a dynamically expandable ring 40 located at a point along the longitudinal length 300 of an implant, such as, for example, at about a medial position on the implant. In FIG. 7A, this embodiment is shown in a relaxed state, prior to or during compression of the ring 40. In FIG. 7B, the embodiment is shown after compression of the threaded expandable ring 40, by insertion of the implant through and into bone tissue, such as by muscular forces or mechanical loading being applied to the implant.

In another embodiment, shown in FIGS. 8A and 8B, a dynamically expandable tip 12 can be attached to an existing bone implant as an accessory tip 45 in order to confer an implant with the ability to resist penetration into bone tissue. In one embodiment, an accessory tip 45 includes, but is not limited to, a threaded boss tip 24, such as shown in FIG. 3B, for screwing into either end of an existing implant, such as, for example, a bone screw, as shown in FIG. 8A. In an alternative embodiment, an accessory tip 45 can be a threaded tapped tip 26, for sliding or screwing, respectively, the accessory tip 45 over either end of an implant, as shown, for example, in FIG. 8B.

FIGS. 8C(i)-8c(v) show further embodiments of the subject invention in which a dynamically expandable tip 12 can be inserted into a bone cavity 204 prior to insertion of a bone screw embodiment 10 and attachment of the screw to bone plate 201. As shown and depicted in FIG. 8C(ii), the tip 12 is formed prior to insertion, and delivered into the bone cavity 204. By contrast, in the embodiment of FIG. 8C(iii) shows a further embodiment in which a liquid, gel or other settable material 205 may be inserted into a bone cavity 204 with an application device 206. Alternatively, the settable material may be applied to the tip of a bone screw 50 that is then inserted, and allowed to set or solidify within the bone 18, as shown in FIGS. 8C(iv) and 8C(v).

Figure 9:
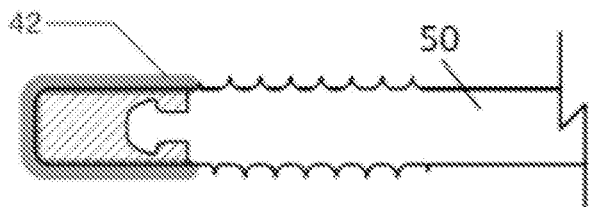
FIG. 9 illustrates one type of embodiment of the current invention: a dynamically expandable coating or sleeve for the distal or proximal ends of existing implants.

FIG. 9 shows a further embodiment in which a dynamically expandable tip 12 is covered by a secondary layer 42 of one or more materials that confer the dynamically expanding tip with additional advantageous properties. For example, a secondary layer can be a spray-on polymer, over-molded polymer, surface treatment, bioactive layer, drug delivery layer, fabric or wire mesh, or any other biocompatible material covering the surface of the tip 12.

Figure 10A:
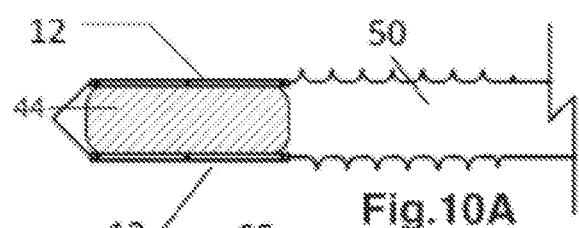
FIGS. 10A, and 10B illustrate embodiments of an implant with a hollow tip that, according to the subject invention, allows a dynamically expandable elastomeric material to be inserted, shown both before FIG. 10A and during FIG. 10B compression.
Figure 10B:
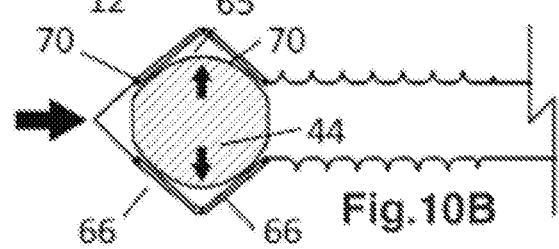

In FIGS. 10A and 10B, an embodiment of the subject invention is shown in which a dynamically expandable tip is in the form of an insert 44 placed within a compressible chamber 65 in a bone implant, where the compressible chamber can have one or more articulating side walls 66. FIG. 10A shows an example of this embodiment in a relaxed state prior to compression of the bone implant. FIG. 10B shows the embodiment during or after compression, in which the compressive forces 21, such as axial forces 14, applied to at or about the tip of the implant are transferred to the dynamically expandable insert, which then translates this compression or axial compression into lateral expansion, as discussed above. This lateral expansion of the expandable tip insert 44 causes the expandable tip insert 44 to press against the articulating side walls 66 of the implant 10 making them also expand laterally, thus creating a contact surface 70 that presses against the bone tissue, thereby resisting forward penetrative movement of the implant.

In an alternative embodiment, the dynamically expandable tip can be in the form of an insert 44 that can be inserted into the distal end 100 of a duct 67 that traverses the entire longitudinal length 300 of the implant. A plug 68 can be inserted into the proximal end 200 of the duct and moved by any of a variety of techniques towards the distal end 100 of the implant. Embodiments of a dynamically expanding tip 12 that utilize one or more dynamically expanding mechanisms 60 have been previously described herein. Such embodiments can operate similarly to the operation of a dynamically expandable insert 44, where lateral expansion causes one or more articulating walls 66 to radiate laterally as well. In FIGS. 11A and 11B, an embodiment of the subject invention is shown that utilizes a spring-loaded mechanism 62 that can mimic the dynamic expansion behavior of an elastomeric polymer material. The expandable mechanism can be constructed such that it provides similar mechanical behavior to that of the elastomeric dynamically expandable tip. In FIG. 11A, it can be seen that with this embodiment in a relaxed state, prior to compression of the bone implant, the shaft 50 is substantially straight and rod-like. In FIG. 11B, it can be seen that, in this embodiment, axial compressive force applied to the tip of the implant is transferred to the one or more dynamically expandable mechanisms 60, which then causes one or more springs or similar devices to translate the this axial compression into lateral expansion. This force of lateral expansion can cause the articulating side walls 66 of the implant, to which the dynamically expandable mechanisms can be attached, to expand or open laterally and form a contact surface to press against the bone tissue, thereby resisting forward penetrative movement of the implant.

Figure 12A:
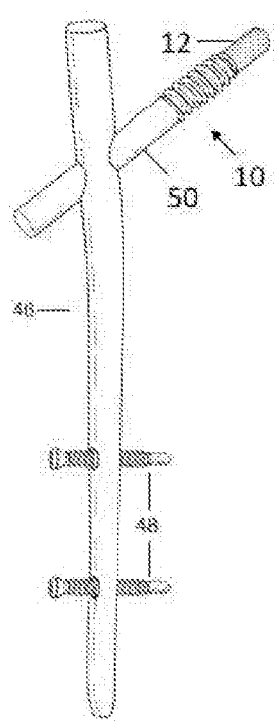
FIGS. 12A, 12B, 12C and 12D illustrate embodiments of a hip screw or nail, according to the subject invention, with a dynamically expandable tip FIG. 12A or ring FIG. 12C as shown both before FIG. 12B and during FIG. 12D compression, respectively.
Figure 12B:
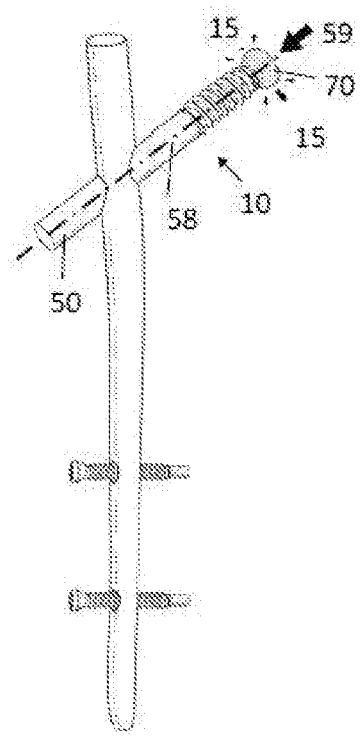
Figure 12C:
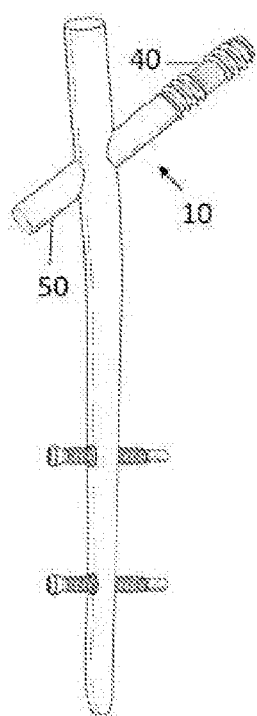
Figure 12D:
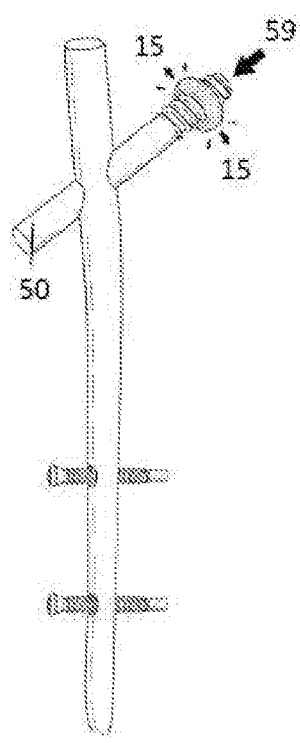

FIGS. 12A-12D show specific embodiments of the current invention in which an implant 10 is used for internal fixation of a fractured hip and includes one or more dynamically expandable tips 12 or rings 40 in order to inhibit unintended or undesirable penetration of bone tissue following implantation. In FIG. 12A, a hip implant can include an embodiment of a dynamically expandable tip 12, which is inserted into the femoral head during fixation surgery. The hip implant can also include one or more bone screws with one or more embodiments of a dynamically expandable tip 12 for attaching the implant to the femoral shaft. In FIG. 12B, a hip implant is shown during compression of the femoral head along the oblique axis 58, as indicated by the force vector arrow 59. The compressive force indicate by the vector arrow 59 is translated into lateral expansion 15 of the dynamically expandable tip 12, resisting further penetration of the implant into the bone tissue of the femoral head. In FIG. 12C, a similar hip implant as described in FIG. 12A is shown, having a dynamically expandable ring 40 in place of the dynamically expandable tip 12. FIG. 12D shows how compression of the distal end of a dynamically expandable ring on the hip implant by compression of the femoral head against the implant is translated into lateral expansion of the ring, resisting further penetration of the implant into the bone tissue of the femoral head. Again, in accordance with the subject invention, expansion of the ring 40 increases the contact area between the ring and adjacent bone tissue, which reduces localised contact stress between the ring and the bone. The reduction of stress in bone adjacent the deformable ring element, which is being urged against the deformable element as provided by the subject invention reduces and inhibits the abovementioned "cut-out" by such stress reduction.

Figure 13A:
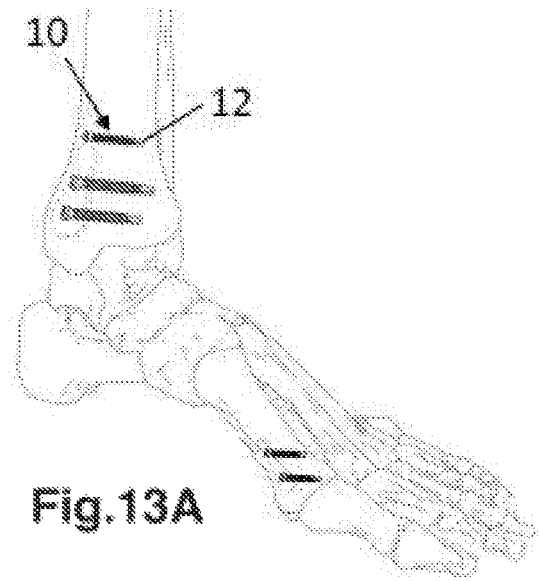
Figure 13B:
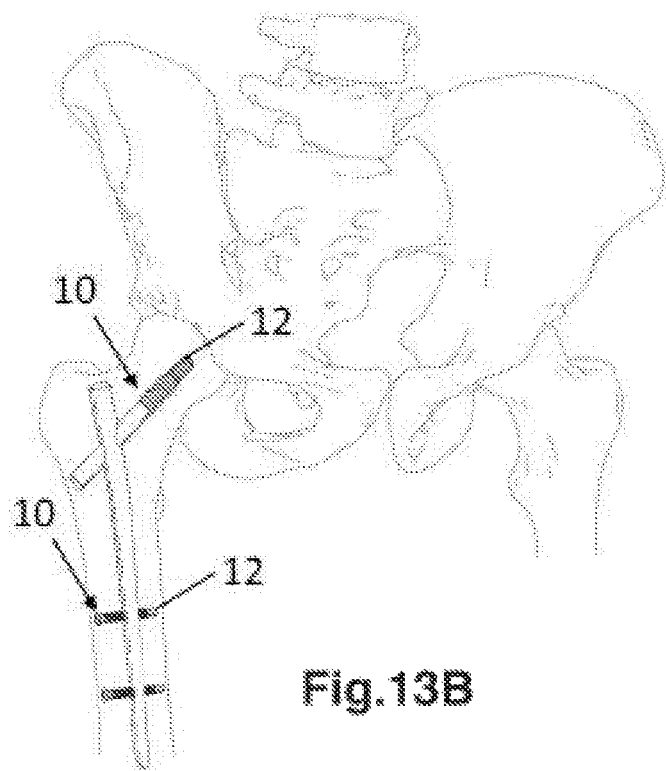
Figure 13F:
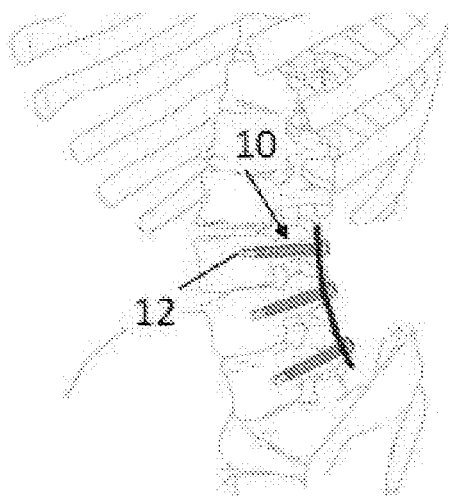
Figure 13G:
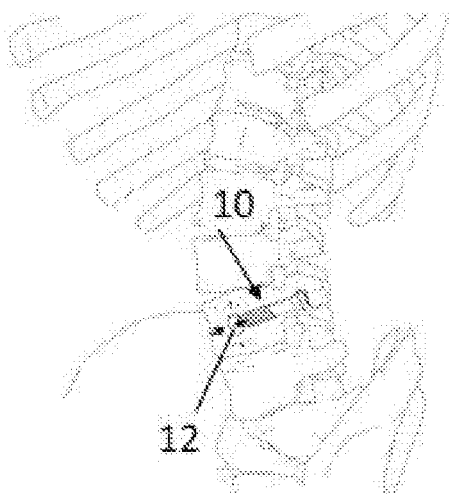
Figure 13H:
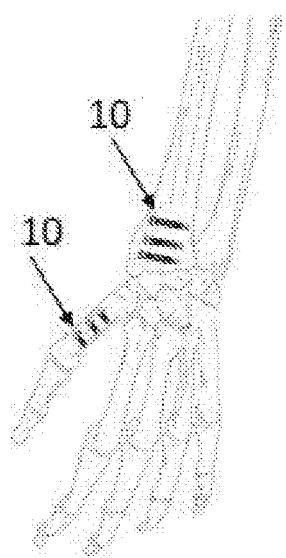

In FIGS. 13A and 13B, there are shown embodiments of the current invention which can be suitable for implantation in bones or bony structures across the human anatomy for fixation of fractures and/or anchoring of tendon or ligament replacements. The embodiments shown in FIGS. 13A and 13B are examples and do not represent all possible locations where embodiments of the subject invention can be implanted, either alone or in combination with other types implants, fixtures, plates or devices in order to suit the treatment of the patient. FIG. 13A presents various bone implants for the lower extremities suitable for in the ankle, foot and/or toes. FIG. 13B shows a hip implant similar to those described in FIGS. 12A through 12D, in an anatomical position for fixation of a hip fracture. In FIG. 13C, embodiments of implants 10, according to the subject invention, are shown for the fixation of fractures of the proximal humerus. In FIG. 13D, embodiments of implants 10, according to the subject invention, are shown for the repair of skull fractures. FIG. 13E shows embodiments of a dental implant in which the distal end 100 features a dynamically expandable tip 12 capable of inhibiting unwanted penetration of the implant into the mandible or skull during chewing. FIG. 13F shows embodiments of implants 10, according to the subject invention, which are suitable for spinal fusion surgery, while FIG. 13G shows how an implant embodiment featuring a dynamically expandable distal tip 12 can be used to decompress vertebral compression fractures by opening cavities in the vertebral body. Such an implant embodiment can be removed or maintained within the vertebral body to provide continuous support while allowing some motion and deformation of the bone, inhibiting unwanted complications such as adjacent vertebral fracture and stress shielding of the bone that often occur in the case of rigid implants. Lastly, FIG. 13H shows embodiments of implants of the subject invention that are suitable for use in the distal radius and/or bones of the hand or fingers.

Figure 14:
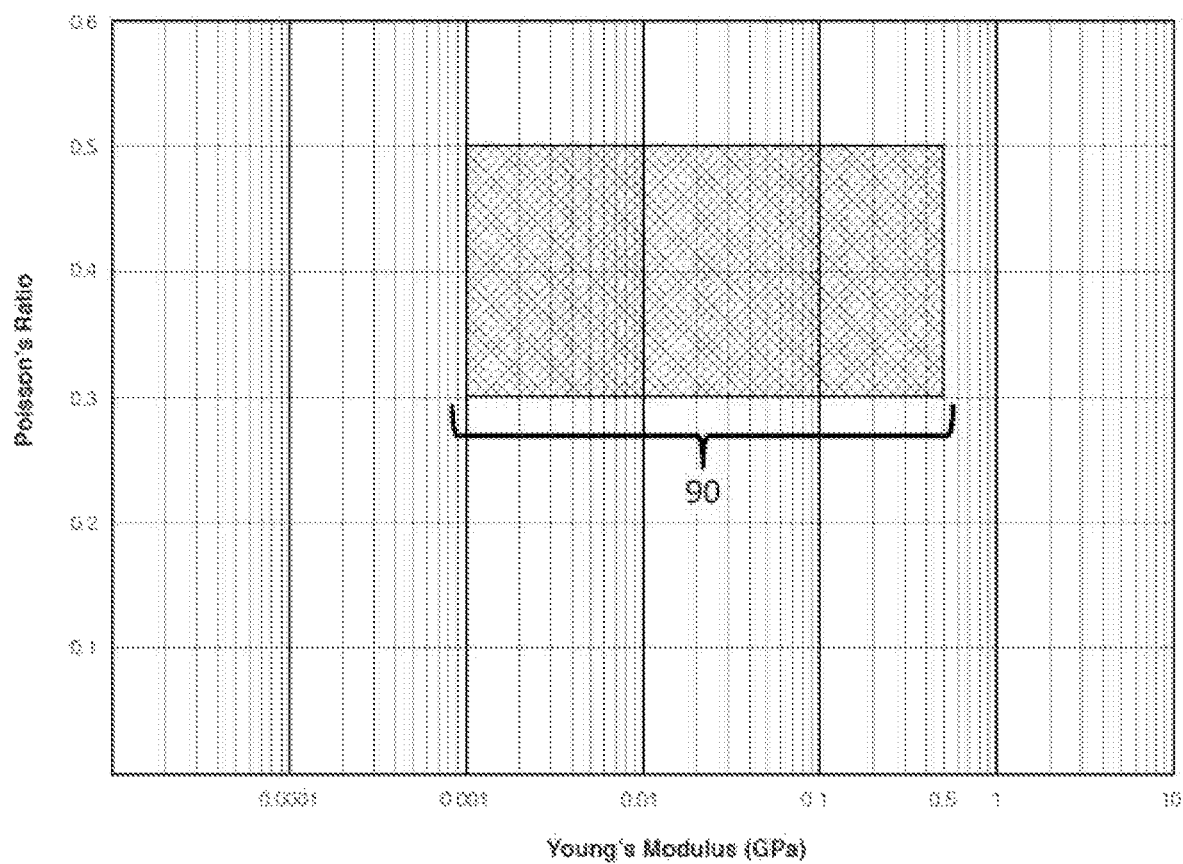
FIG. 14 is a graph that illustrates the region inhabited by the elastomeric polymer materials that can be utilized in fabrication of the dynamically expanding features employed with embodiments of the subject invention. As shown, materials with Poisson's Ratios of from 0.3 to 0.5 and Young's Moduli of from 0.001 GPa to 0.5 GPa are examples of a materials with suitable mechanical characteristics for the embodiments of the subject invention.

FIG. 14 is a diagram that defines a region 90 on the graph of Poisson's Ratios From 0.3 to 0.5) and Young's Moduli From 0.001 GPa to 0.5 GPa) that include materials that can be suitable for construction of embodiments of a dynamically expandable tip 12 as described herein. Alternatively, there can be used dynamically expanding mechanisms 60 and/or composites of other materials that can mimic a dynamically expanding tip having the ranges of properties indicated in FIG. 14. With respect to FIG. 14 and the material from which the expandable tip 12 can be formed therefrom, physical parameters which define the boundary conditions in this regard include:

(i) size of expandable tip in view of surgical application, in view of anatomical dimensions, and applicability of size of the implant from a clinical standpoint,
(ii) mechanical properties of surrounding bone stock, including allowance of diseased cancellous bone having deceased mechanical properties and integrity, including reduced or altered modulus and compression stress
(iii) physical loading depending upon anatomical application and external load force.

As will be appreciated by those skilled in the art, parameters including the above dictate the material properties of an expandable tip 12, in combination with physical size of the tip, such that sufficient lateral expansion is proved by the expandable tip 12, so as to cause a sufficient increase in contact area between the expandable tip 12 and adjacent bone such that the stress in the adjacent bone is reduced so as to reduce or mitigate penetration of the expandable tip into the adjacent bone, thus reducing "cut-out", in accordance with the present invention. Accordingly, examples as provided are not restrictive, however include materials properties for which, when incorporated in the present invention as an expandable tip 12 of appropriate sizing for anatomical placement, may achieve the requisite expansion effect in accordance with the invention.

Example 1: Porcine Bone Penetration Test

Figure 15A:
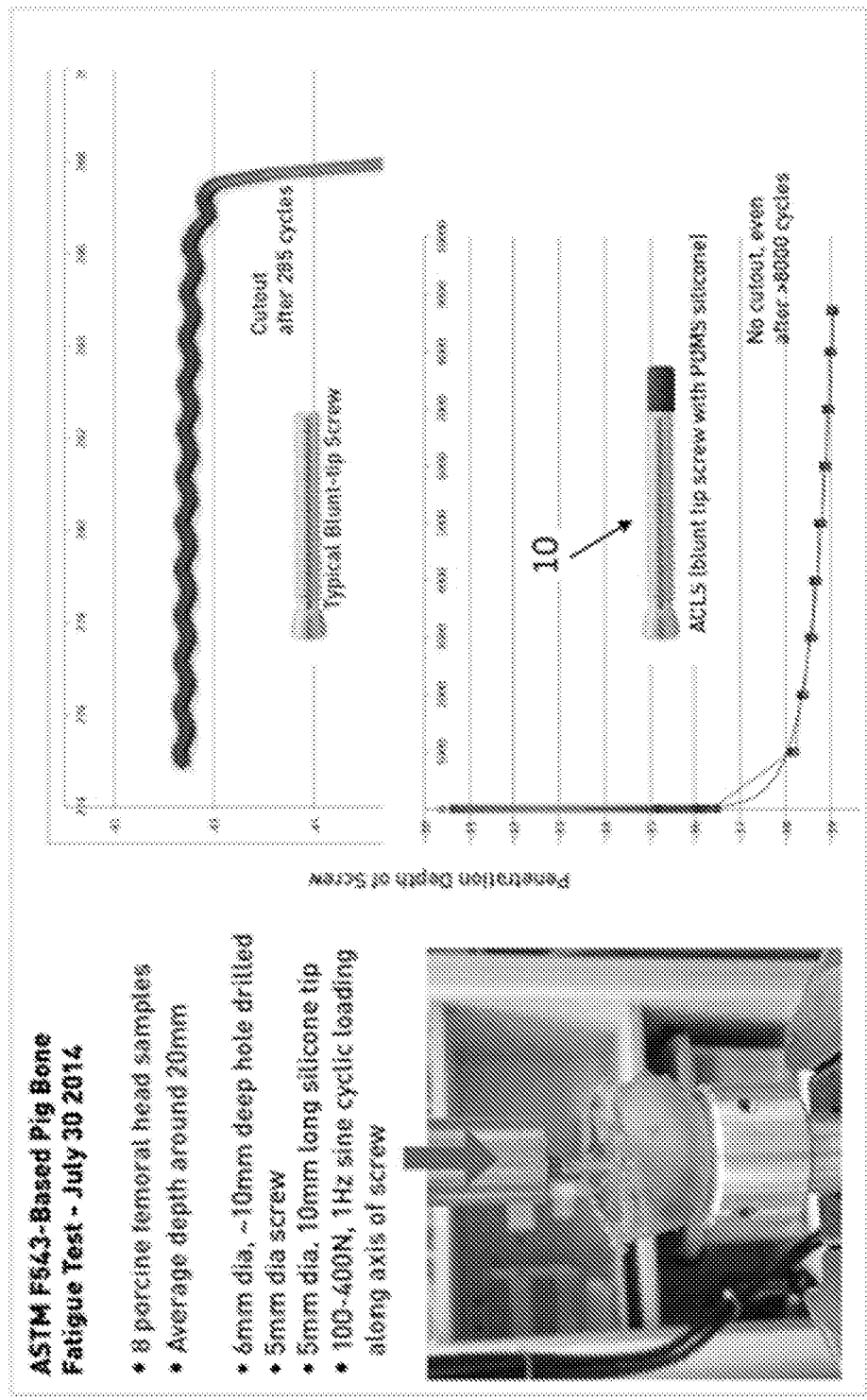

In FIG. 15A, there is shown the results of porcine bone penetration experiments, comparing the rates of penetration of bone screws featuring dynamically expanding tips with the rates of penetration of conventional blunt-tipped bone screws. These experiments, conducted by the inventors under controlled laboratory conditions based on standards detailed in ASTM F543, tested the penetration rate of 5 mm diameter bone screws placed in shallow 6 mm diameter pilot holes drilled into the surfaces of fresh porcine femoral heads. Each screw type (either conventional blunt-tipped steel alloy or steel alloy with dynamically expandable tip of silicone rubber foam), was loaded axially by biomechanical testing machine with a sinusoidal load of 100-400N at 1 Hz, until penetration of the screw through the bone tissue was recorded (representing approximately 1.5 cm of bone penetration). Over the course of 8 testing cycles for each screw type, the rate of penetration of the bone screw with dynamically expandable tip was shown to be at least 0.025 the rate of a conventional blunt-tipped screw.

Example 2: Artificial Bone Penetration Test 1

In FIG. 15B, there is shown the results of artificial bone penetration experiments, comparing the rates of penetration of bone screws featuring dynamically expanding tips with the rates of penetration of conventional blunt-tipped bone screws. These experiments, conducted by the inventors under controlled laboratory conditions based on standards detailed in ASTM F543, tested the penetration rate of 5 mm diameter bone screws placed in shallow 6 mm diameter pilot holes drilled into artificial bone testing material consisting of polyurethane foam blocks with a density of 0.16 g/cc (PU Block #10 produced by Sawbones™, Inc.). Each screw type (either conventional blunt-tipped steel alloy or steel alloy with dynamically expandable tip of silicone rubber foam), was loaded axially by biomechanical testing machine with a sinusoidal load of 50-135N at 1 Hz, until penetration of the screw through the artificial bone was recorded (representing approximately 1.0 cm of artificial bone material penetration). Over the course of 8 testing cycles for each screw type, the rate of penetration of the bone screw with dynamically expandable tip was shown to be approximately 0.01 the rate of a conventional blunt-tipped screw.

As mentioned above, the dynamically expandable tip can be an insert 44 within the distal end 100 of a duct 67 through longitudinal length 300 of the implant. A plug 68 can be inserted into the opposite or proximal end 200 of the duct and moved by any of a variety of techniques towards the distal end 100 of the implant. FIG. 16A illustrates one non-limiting example of an embodiment that utilizes a plug to adjust the amount of the dynamically expandable tip insert 44 that extends from the distal end of the implant. FIG. 16B illustrates an example of this embodiment, where the duct and the plug have compatible threading that allows the plug to be incrementally adjusted by screwing the plug into the duct, so as to push the plug towards the distal end and control the length of the dynamically expandable tip extending at the distal end of the shaft.

FIGS. 17A, 17B, and 17C(i)-17C(iii) illustrate one embodiment of an implant 10, according to the subject invention, which is a bone screw or rod, that can be used for internal fixation of fractures and having a deformable element as a dynamically expandable tip. In FIG. 17A there is shown a bone screw or rod 10, featuring a threaded proximal end 207, shaft 50, and threaded distal end 11, with an attached dynamically expandable distal tip 12, prior to insertion within a predrilled hole 204 in a segment of bone tissue 18. A bone plate with tapped hole 201 is positioned proximal to the opening of the predrilled hole 204, such that the bone screw 10 must pass through the tapped hole in order to enter the bone tissue 18, as shown in FIG. 17B. FIG. 17C(i) further illustrates, in partial section view, an example of this embodiment in a relaxed state following implantation into the bone tissue, but prior to the application of physiological loading or compression. FIG. 17C(i) further illustrates the insertion of a bone screw 10 into bone tissue 18 while undergoing a turning motion in order to engage its proximal threads 207 with the tapped hole in the bone plate 201. The turning motion during insertion also aids in the engagement of the distal threads 11 of the bone screw 10 with the perimeter walls of the predrilled hole 204 of the distally located bone tissue 208 so as to urge such tissue in the proximal direction and thereby aid in fixation of the bone fracture 214.

Following implantation of a bone fixation device within living bone tissue, changes in bone composition, strength and bone health can occur that alter the mechanical integrity of the bone tissue over time. Examples of such changes include, but are not limited to, bone remodeling, bone ageing, surgical revision complications, loss of bone mass, the onset or progression of osteoporosis, or stress shielding.

As a result of such loss or alteration of mechanical integrity of the bone tissue, physiological loading of the fractured bone can lead its collapse. As shown in FIG. 17C(ii), loading of the more distally located bone tissue 208 by an axial compression force 14 may cause it to be urged toward the proximally located bone tissue 215 such that partial collapse or crushing 209 of the bone tissue occurs. Upon being urged proximally, the distal bone tissue 208 thereby proximally urges the dynamically expandable tip 12 such that the axial compression force 14 is translated into lateral expansion force 15, due to the material properties (e.g., Poisson's Ratio and Young's Modulus) or mechanical configuration (e.g., a spring-loaded mechanism, such as depicted in FIGS. 11A and 11B) of the distally, or approximately distally, located 100 dynamically expanding tip 12. In accordance with embodiments of the subject invention, deformation of the tip 12 increases the contact area 17 between the tip 12 and adjacent bone tissue, which reduces localised contact stress 211 between the tip 12 and the bone. The reduction of stress in bone adjacent to the deformable element, which is being urged against the deformable element as provided by the subject invention, inhibits the abovementioned "cut-out" by such stress reduction. As an additional effect, when an implant 10 embodiment of the subject invention has been placed in bone, the lateral expansion force 15 of the dynamically expanding tip 12 can increase the kinetic force of friction with the bone tissue. This can occur because during compressive force 21, there is formed at least one enlarged contact surface 70 on the dynamically expanding tip 12 that presses against the bone tissue and can resist an axial compressive force 14 applied by the bone tissue as seen in FIG. 17C(ii). This contact surface, which provides increased frictional force 17, can resist further penetration of an implant, such as a bone screw embodiment, past the point of the implant location, while allowing for small magnitude movements of the bone with minimal damage to the bone tissue.

FIG. 17C(iii) shows an example of the dynamically expandable tip 12 restored to the original, or almost the original, un-deformed shape after cessation of the axial compression force 14. Due to its elastic (i.e., spring-like) properties, the dynamically expandable tip 12 can assist in the restoration of its own original shape by exerting a distally directed spring force 210 on the distally located bone tissue 208. After cessation of forces as shown, in the event screw removal is required, this may be effective in helping to remove the screw through the original opening.

Figure 18:
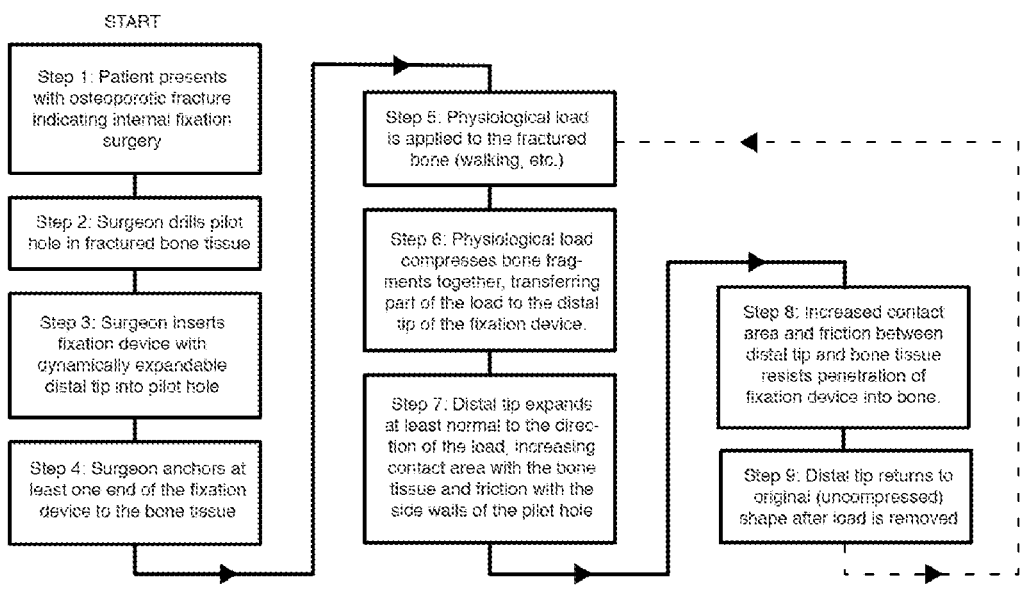
FIG. 18 shows a flowchart representing the steps of one example for the process of how the current invention can may usefully resist bone tissue penetration following surgical implantation in a fractured bone.
Figure 19A:
FIGS. 19A-19H illustrate methods and techniques by which a dynamically expandable tip that is cannulated (i.e., includes a through hole) can be attached to the distal end of a cannulated bone implant such as a cannulated bone screw.
Figure 19B:
Figure 19C:
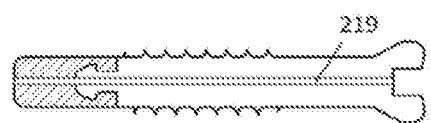
Figure 19D:
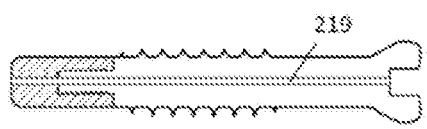
Figure 19E:
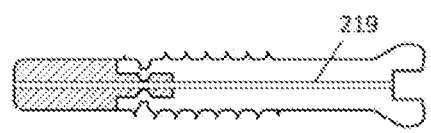
Figure 19F:
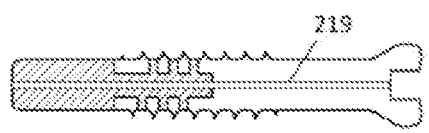
Figure 19G:
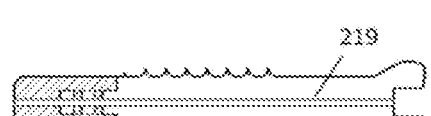
Figure 19H:
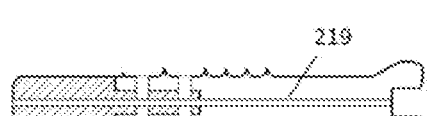
Figure 20A:
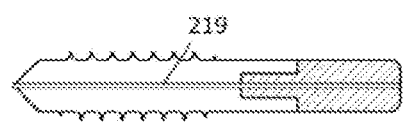
FIGS. 20A-20H illustrate further methods and techniques by which a dynamically expandable tip that is cannulated (i.e., includes a through hole) can be attached to the proximal end of a cannulated bone implant such as a cannulated bone screw.
Figure 20B:
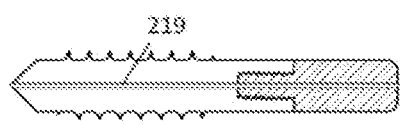
Figure 20C:
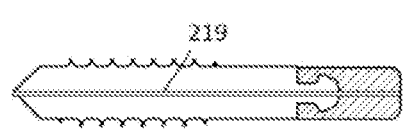
Figure 20D:
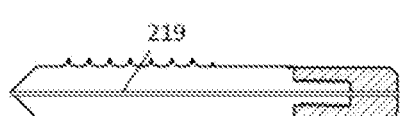
Figure 20E:
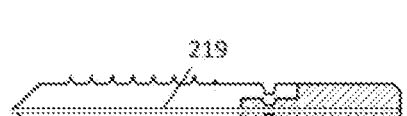
Figure 20F:
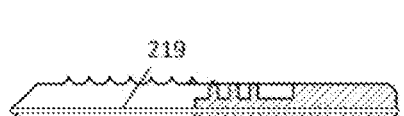
Figure 20G:
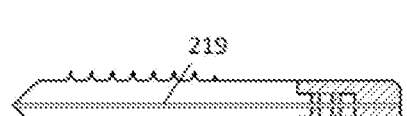
Figure 20H:
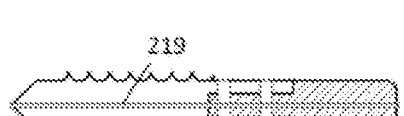

FIG. 18 shows a flowchart representing the steps of one non-limiting example of the process of using a fixation device embodiment of the current invention to resist bone tissue penetration following surgical implantation in a fractured bone. In Step 1, a patient presents with an osteoporotic fracture indicating internal fixation surgery, for example, but not limited to, a neck fracture 19 of the proximal humerus as illustrated in FIGS. 2A and 2B, or the fracture 214 illustrated in FIGS. 17C(i)-17C(iii). In Step 2, the surgeon drills a hole in the fractured bone tissue, as illustrated by pilot hole 204 in FIGS. 17A-17C. In Steps 3 and 4, the surgeon inserts the fixation device with a dynamically expandable distal tip into the pilot hole and anchors at least one end of the device to the bone tissue, as illustrated in FIGS. 2A and 17C(i). In Steps 5 and 6, physiological loading of the bone tissue, shown as 14 and 21 in FIGS. 2B and 17C(ii), compresses the bone fragments or regions of bone tissue 208 and 215 together, transferring part of the load to the distal tip 12 of the fixation device. In Step 7, the distal tip 12 expands 15 with a force at least normal to the direction of the load 14 and 21, increasing contact area 70 with the bone tissue and force of kinetic friction with the sidewalls of the pilot hole 204. In Step 8, the increased contact area and friction between distal tip and bone tissue resists penetration of fixation device into bone, thereby reducing the incidence of unwanted penetration-related complications. Finally, in Step 9, following the cessation of the compressive force 14, the distal tip returns to its original, or nearly original, shape, as shown in FIG. 17C(iii).

As in FIGS. 3A-3H, FIGS. 19A-19H illustrate various non-limiting methods and techniques for attaching an embodiment of a dynamically expanding tip 12 formed as an end piece 20 of elastic or deformable material to the distal end of an implant, such as, for example, a bone screw similar to the embodiment of a bone screw with dynamically expanding tip depicted in FIG. 1. Each variant shown in FIGS. 19A-H corresponds to the similar letter-designation variant shown in FIGS. 3A-4H, with the exception that a through hole 219 is added such that the screw is cannulated and may, for example, by implanted with the guidance of a guide wire.

As in FIGS. 4A-4H, FIGS. 20A-20H illustrate various non-limiting methods and techniques for attaching an embodiment of a dynamically expanding tip 12 formed as an end piece 20 of elastic or deformable material to the proximal end of an implant, such as, for example, a bone screw similar to the embodiment of a bone screw with dynamically expanding tip depicted in FIG. 1. Each variant shown in FIGS. 20A-H corresponds to the similar letter-designation variant in FIGS. 4A-4H, with the exception that a through hole 219 is added such that the screw is cannulated and may, for example, by implanted with the guidance of a guide wire.

FIGS. 21A(i)-21A(iii) illustrate one embodiment of an implant 213, according to the subject invention, such as, by way of non-limiting example, a bone screw or rod, that can be used for internal fixation of fractures and consisting entirely of a deformable material such as an elastomeric polymer. As illustrated in FIG. 21A(i), dynamically expanding implant 213 is implanted within the pilot hole 204 of the fractured bone tissue 18 such that it passes through fracture 214 and is attached at its proximal end to bone plate 201. Following implantation of such a bone fixation device within living bone tissue, changes in bone composition, strength and bone health may occur that alter the mechanical integrity of the bone tissue over time. Examples of such changes include, but are not limited to, bone remodeling, bone ageing, surgical revision complications, loss of bone mass, the onset or progression of osteoporosis, or stress shielding. As a result of such loss or alteration of mechanical integrity of the bone tissue, physiological loading of the fractured bone may lead its collapse. As shown in FIG. 21A(ii), loading of the more distally located bone tissue 208 by an axial compression force 14 may cause it to be urged toward the proximally located bone tissue 215 such that partial collapse or crushing 209 of the bone tissue occurs. Upon being urged proximally, the distal bone tissue 208 thereby proximally urges the distal, or approximately distally located, portion of dynamically expanding implant 213 such that the axial compression force 14 is translated into lateral expansion force 15, due to the material properties (e.g., Poisson's Ratio and Young's Modulus) or mechanical configuration (e.g., a spring-loaded mechanism, such as depicted in FIGS. 11A and 11B) of dynamically expanding implant 213. In accordance with the subject invention, deformation of the distal, or approximately distally located, portion of dynamically expanding implant 213 increases the contact area 17 between the tip 12 and adjacent bone tissue, which reduces localised contact stress 211 between the deformable implant 213 and the bone. The reduction of stress in bone adjacent the deformable implant which is being urged against the deformable element as provided by the subject invention and inhibits the above-mentioned "cut-out" by such stress reduction. As an additional effect, when an implant 10 embodiment of the subject invention has been placed in bone, the lateral expansion force 15 of the dynamically expanding implant 213 can increase the kinetic force of friction with the bone tissue. This can occur because during compressive force 21, there is formed at least one enlarged contact surface 70 on the dynamically expanding implant 213 that presses against the bone tissue and can resist an axial compressive force 14 applied by the bone tissue as seen in FIG. 17C(ii). This contact surface, which provides increased frictional force 17, can resist further penetration of an implant, such as a bone screw embodiment, past the point of the implant location, while allowing for small magnitude movements of the bone with minimal damage to the bone tissue.

FIG. 21A(iii) shows the dynamically expandable implant 213 restored to the original, or almost the original, undeformed shape after cessation of the axial compression force 14. Due to its elastic (i.e., spring-like) properties, the dynamically expandable implant 213 can assist in the restoration of its own original shape by exerting a distally directed spring force 210 on the distally located bone tissue 208. After cessation as shown, in the event screw removal is required, this may be effective in removing the screw through the original opening in the bone.

FIG. 22A depicts a representative sample of the internal structure of bone tissue within load-bearing long bones such as the humerus or femur, showing, in particular, the presence of deep pores and cavities. FIG. 22B illustrates one possible embodiment of the current invention in the form of a bone screw 10 placed in proximity to bone tissue 18. For the purpose of illustration, an example of the porous surface 212 of such bone tissue is shown at somewhat exaggerated scale. As shown in FIG. 22C, physiological loading of the bone tissue, shown as 14 and 21 in FIGS. 2B and 17C(ii), urges the porous surface 212 of the bone tissue towards the proximal end of the implanted fixation device, transferring part of the load to the distal tip 12 of the fixation device. The distal tip 12 thereby expands 15 with a force at least normal to the direction of the load 14 and 21, increasing contact area 70 with the bone tissue. Likewise, the tip 12 expands under load, such that numerous fingers or projections of tip material 220 can partially occupy vacancies in the porous surface 212, further increasing the contact area with the bone tissue and thereby resisting penetration of the implant into the bone.

The present invention, by provision of deformable tip or tip portion, provides advantages over prior art, as well as reduces the likelihood or ameliorates "cut-out", a problem associated with devices of the prior art. Such a deformable tip or tip portion assists in overcoming such deficiencies by expanding in a manner so as to resist and prevent "cut-out". Aspects of the deformable tip or tip portion which assist in achieving such advantages include:

(i) deformation and expansion of the tip, so as to decrease localized stresses in the bone adjacent the tip
(ii) deformation and expansion of the tip so as to permit expansion into the pores and cavities present in osteoporotic cancellous bone tissue, thereby further increasing the contact area between implant and bone tissue
(iii) deformation and expansion of the tip may increase frictional force between the tip and bone tissue and further resist penetration of the bone screw into the bone tissue.

In alternative embodiments, the present invention, by provision of deformable side or side portion(s), provides advantages over prior art, as well as reduces the likelihood or ameliorates aseptic loosening, stress shielding, or "cut-out" or unwanted penetration in directions oblique or lateral to the long axis, problems associated with devices of the prior art.

Similarly to the deformable tip portion as discussed, the deformable side or side portion(s) assist in overcoming such deficiencies by expanding in a manner so as to resist and prevent "cut out" or unwanted penetration of the device, localized excessive loading, as well as stress shielding and/or aseptic loosening. Aspects of the deformable side or side portion(s) which assist in achieving such advantages include:

(i) deformation and expansion of the side or side portion(s) responsive to physiological loading, so as to decrease localized stresses in the bone adjacent the side or side portion(s)
(ii) deformation and expansion of the side or side portion(s) responsive to physiological loading, so as to permit at least expansion into the pores and cavities present in osteoporotic cancellous bone tissue, thereby further increasing the contact area between implant and bone tissue
(iii) deformation and expansion of the side or side portion(s) responsive to physiological loading, may increase frictional force between the side or side portion(s) and bone tissue and further resist penetration of the bone screw into the bone tissue.

In such alternative embodiments, a dynamically expandable side or lateral portion a fixation device is provided which includes a deformable structure that includes one or more elastomeric polymers, for example having a Poisson Ratio of from 0.3 to 0.5 and for example a Young's Modulus of from 0.001 GPa to 0.5 GPa.

Such elastomeric polymers can include, but are not limited to, saturated and unsaturated natural and artificial rubbers and foams such as polyisoprene, fluorinated polymers, brominated polymers, chloroprenes, butyl rubbers, styrene-butadiene rubbers, nitrile rubbers, ethylene-propylene rubbers, epichlorohydrin rubbers, silicone, silicone rubbers, polydimethylsiloxane, fluorosilicone rubbers, fluoroelastomer rubbers, perfluoroelastomer rubbers, polyvinyl alcohol, polyvinyl acetate, polyvinyl chloride, polycaprolactone, polylactic acide, ethyl-vinyl acetate, latex rubbers, collagens, thermoplastic elastomers, proteins such as resilin and elastin, elastolefin and polysulfide rubbers. In a specific embodiment, a dynamically expanding side or lateral portion 400 is formed from a Polydimethylsiloxane (PDMS), a type of silicone rubber suitable for implantation into a body.

A dynamically expanding side or lateral portion can also employ one or more dynamically expanding mechanisms 401, such as, for example, those including a system of springs or cams, as shown in FIG. 39 that are mechanically configured to approximate the behavior of elastomeric polymers which is discussed further below.

These dynamically expanding mechanisms can be fabricated or formed from relatively rigid materials, including, but not limited to, metal alloys, such as steel, titanium and aluminum alloys, ceramics, or rigid polymers, or a combination of such rigid materials with flexible or elastic materials, such as elastomeric polymers, spring steels, nylon, and nitinol. Composites that include one or more elastomeric materials and/or one or more rigid materials can also be employed so as to have a low overall stiff, so as to deform under load in situ, in a manner so to be expandable and provide resistance to migration of the device within bone. Such an expanding mechanism would provide suitable deformation under applicable physiological load as to that as provided by an elastic or elastomeric material which materials properties for example, a Poisson Ratio of from 0.3 to 0.5 and for example a Young's Modulus of from 0.001 GPa to 0.5 GPa.

Figure 23:
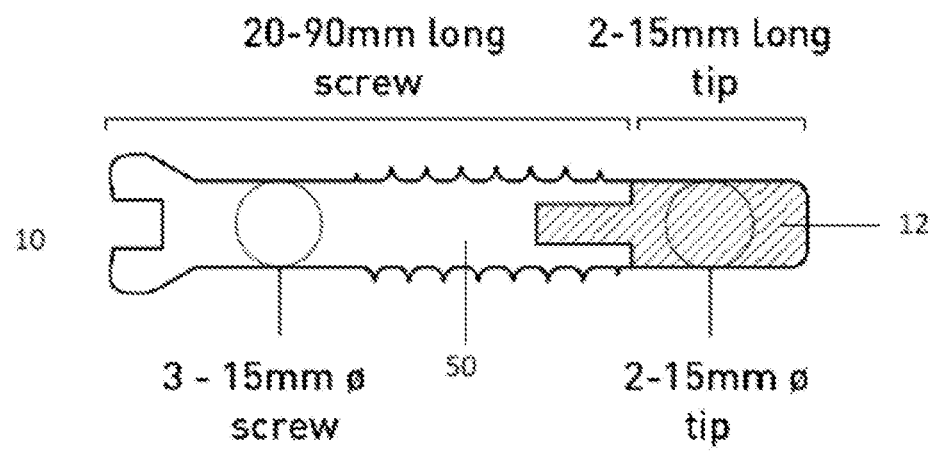
FIG. 23 illustrates several possible ranges of the length and diameter of a bone screw implant embodiment of the current invention that are suitably sized for anatomical placement within the bone of a subject.

An example of a suitably sized screw type implant is shown in FIG. 23 for anatomical placement within the bone of a subject. In this example, the screw 50 length is the range 20-90 mm and preferably 50 mm, while its diameter is in the range of from 3-15 mm and preferably 5 mm. The expandable tip 12 length is in the range 2-15 mm, and its diameter is in the range from 2-15 mm and preferably 4.5 mm. The screw 50 is formed from a biocompatible and corrosion-resistant metal alloy, preferably stainless steel, titanium or cobalt-chromium alloy, and the expandable tip 12 is formed from elastomeric polymer, preferably medical grade PDMS silicone rubber or polyurethane rubber, although in other embodiments other materials may be used without departing from the scope of the invention.

Figure 24:
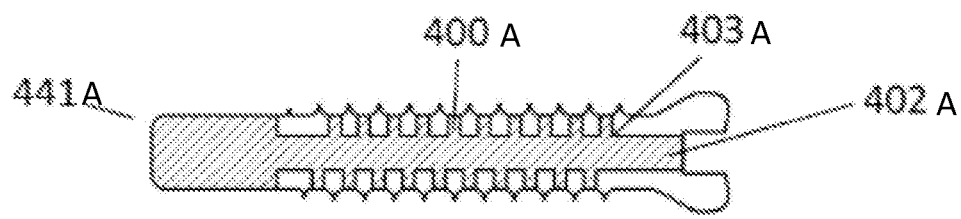
FIG. 24 illustrates an embodiment of a bone screw of the current invention having dynamically expandable portions along the disposed along the longitudinal length of the screw

FIG. 24 illustrates an embodiment of a bone screw 441A of the current invention having dynamically expandable portions 400 in the form, for example, as fingers, feet, or other small protrusions 400A, located along the length of the implant. As shown, an expandable material like an elastomer 402A that is molded within the core of the bone screw may form these dynamically expandable features 400A on the side of the implant by protruding at intervals through holes 403 in the body of the screw 441A. This figure illustrates an embodiment in which the expandable material protrudes at regular intervals between the thread features of the bone screw 441A.

Figure 25:
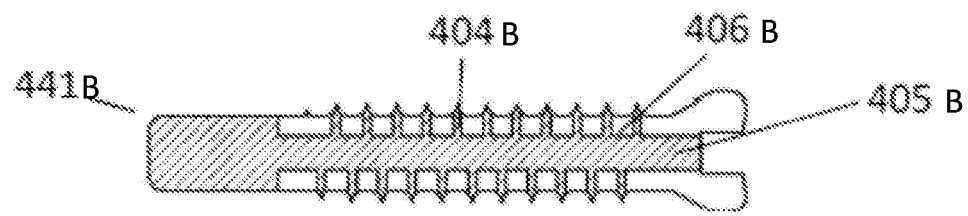
FIG. 25 illustrates another embodiment of a bone screw of the current invention with dynamically expandable portions disposed along the longitudinal length of the screw.

FIG. 25 illustrates a further embodiment of a bone screw 441B of the current invention with dynamically expandable portions 404B provided as fingers, feet, or other small protrusions 404B, located along the length of the bone screw 441B. As shown, an expandable material such as an elastomer 405B that is molded within the core of the bone screw 441B may form these dynamically expandable portions 404B on the side of the bone screw 441B by protruding at intervals through holes 406B in the body of the bone screw 441B. This figure illustrates and embodiment in which the expandable material protrudes at regular intervals at the vertices or apexes of the thread portion features of the bone screw 441B.

FIGS. 26A and 26B illustrate two configurations of two embodiments of a bone screw 441C with dynamically expandable side or lateral portion(s) 407C, distal tip 408C, and core 409C with dynamically expandable portion features in an un-deployed configuration.

The core of this bone screw 441C has a hollow portion 410C. Also, the dynamically expandable side or lateral portion(s) 407C are located at or beneath the surface of the bone screw 441C, allowing the bone screw 441C to be inserted into a bony body without damaging or tearing the expandable portion features 407C.

FIG. 26B illustrates a method for urging the dynamically expandable side or lateral portion(s) 407C of FIG. 26A outward in a direction 425C away from the core 409C of the bone screw 441C by inserting a threaded rod or other instrument 412C into the hollow portion 410C of the bone screw core 441C. Following insertion of the bone screw 441C into a bony body, the threaded rod 412C may be pushed or screwed into the hollow portion 410C of the bone screw core, compressing the inward-facing side 413C of the expandable material and thereby urging the dynamically expandable side or lateral portion(s) 407C and distal tip through the holes 414C in the bone screw 441C located between the thread portion features of the bone screw 415 and in an outward direction 425 into the surrounding bone tissue. This and similar methods of urging the such portion features 407C outwards through holes in the side of the bone screw 441C may be used to stabilize the bony body, as well as the position of the bone screw 441C relative to the bony body.

FIGS. 27A and 27B illustrate two configurations of an embodiment of a bone screw 441D with dynamically expandable side or lateral portion(s) 416D, distal tip 417D, and core 418D, with dynamically expandable portion features 416D in an un-deployed configuration.

The core 418D of this embodiment of bone screw 441D is partially hollow 419D. Also, the dynamically expandable side or lateral portion(s) 416D are located at or beneath the surface of the bone screw 441D, allowing the bone screw 441D to be inserted into a bony body without damaging or tearing the expandable portion features 416D. FIG. 27B illustrates a method for urging the dynamically expandable side or lateral portion(s) 416D of FIG. 27A outward in a direction 426D away from the core of the bone screw 441D by inserting a threaded rod or other instrument 421D into the hollow portion 419D of the bone screw core 418D.

Following insertion of the bone screw 441D into a bony body, the threaded rod 421D may be pushed or screwed into the hollow portion 419D of the bone screw core 418D, compressing the inward-facing side 422D of the expandable material and thereby urging the dynamically expandable side or lateral portion(s) and distal tip through the holes 423D in the bone screw located at or in the thread features of the bone screw 424D and in an outward direction 426D into the surrounding bone tissue. This and similar methods of urging such expandable portion features 416D outwards through holes in the side of the bone screw 441D may be used to stabilize the bony body, as well as the position of the bone screw 441D relative to the bony body.

Figure 28A:
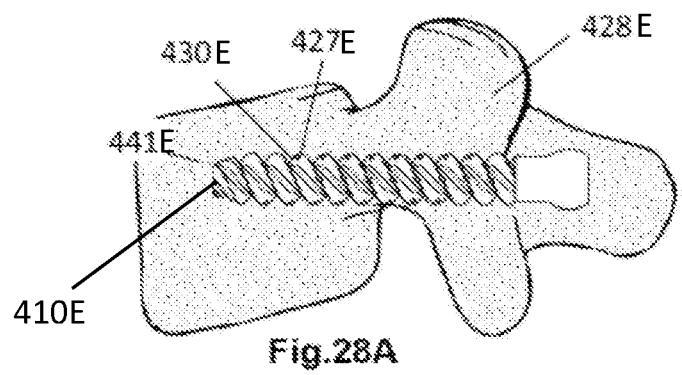
FIGS. 28A and 28B illustrate two configurations of an embodiment of a bone screw embodiment of the current invention for implantation in the vertebrae of a subject and having dynamically expandable side or lateral portion(s) and core similar to what is illustrated in FIG. 25, whereby FIG.
Figure 28B:
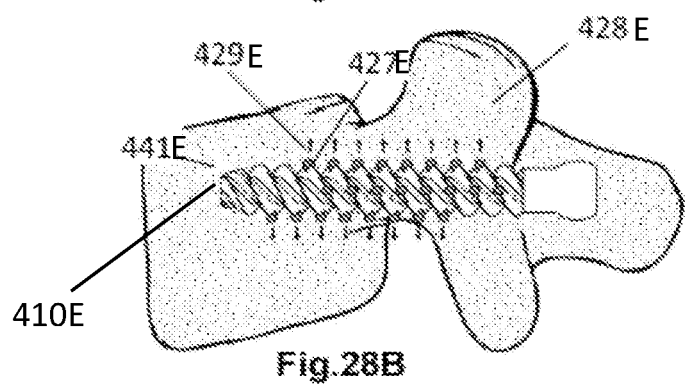

FIGS. 28A and 28B illustrate two configurations of an embodiment of a bone screw 441E for implantation in the vertebrae of a subject with dynamically expandable side or lateral portion(s) 427E and core 410E. FIG. 28A illustrates the bone screw 441E following implantation in a vertebra through the pedicle 428E, with dynamically expandable side or lateral portions(s) 427E in an un-deployed configuration. Such a bone screw 441E may be used for repair of a vertebral fracture and/or anchoring within a vertebra for the purpose of providing support to a fixation device, such as illustrated in FIGS. 30A-30C and FIG. 31 as discussed below. FIG. 28B illustrates a configuration in which the dynamically expandable side or lateral portion(s) 427E have been deployed, using a mechanism such the threaded rod as described in reference to FIGS. 26A-26B and FIGS. 27A-27B to urge such portion features 427E in an outward direction 429 from the core 410E through holes 430E in the bone screw 441E and into the surrounding bone tissue. This and similar methods of urging such portion features 427E outwards through holes in the side of the bone screw 441E may be used to stabilize the bony body, as well as the position of the bone screw 441E relative to the bony body.

Figure 29A:
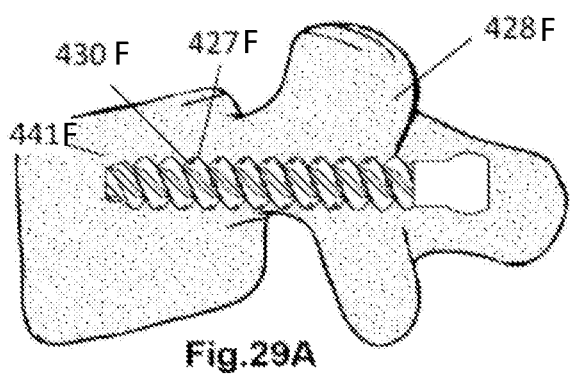
FIGS. 29A and 29B illustrate two configurations of an embodiment of a bone screw embodiment of the current invention for implantation in the vertebrae of a subject and having dynamically expandable side or lateral portion(s) and tip portion and core similar to what is illustrated in FIG. 25, whereby
Figure 29B:
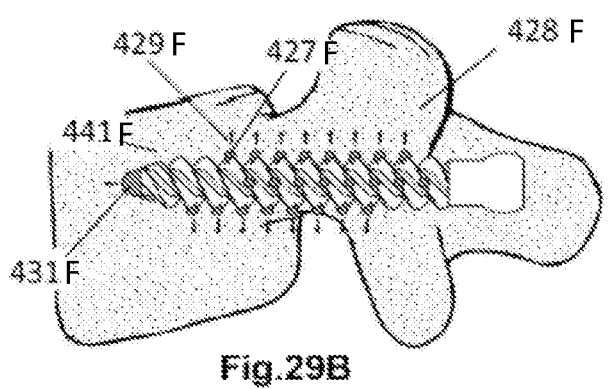

FIGS. 29A and 29B illustrate two configurations of an embodiment of a bone screw 441F for implantation in the vertebrae with dynamically expandable side or lateral portion(s) 427F, distal tip 431F, and a core. FIG. 29A illustrates one such bone screw 441F following implantation in a vertebra through the pedicle 428, with dynamically expandable side and lateral portion(s) 427F and tip 431F in an un-deployed configuration. Such a bone screw 441F may be used for repair of a vertebral fracture and/or anchoring within a vertebra for the purpose of providing support to a fixation device, such as illustrated in and described with reference to FIGS. 30A-30D and FIG. 31.

FIG. 29B illustrates a configuration in which the dynamically expandable side or lateral portion(s) 427F and distal tip 431F have been deployed, using a mechanism such the threaded rod 412 or 421 described in FIGS. 26A-26B and FIGS. 27A-27B to urge such expandable portion 427F features outwards 429F through holes in the bone screw 441F and into the surrounding bone tissue. This and similar methods of urging such expandable portion features 427F outwards through holes in the side of the bone screw 441F may be used to stabilize the bony body, as well as the position of the bone screw 441F relative to the bony body.

FIGS. 30A, 30B, 30C and 30D illustrate two configurations of an embodiment of same bone screws 441G according to the current invention in which said bone screws 441G are used as anchors for a flexible vertebral support device 436G. Such bone screws are often termed pedicle screws in relation to spinal fixation and spinal fusion type applications.

Figure 30A:
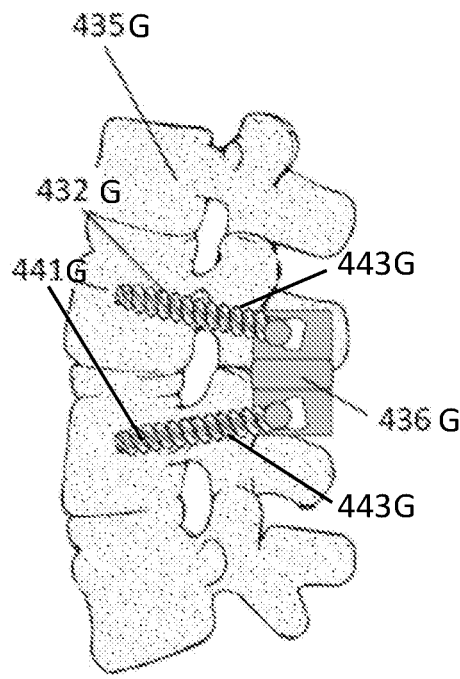
FIGS. 30A, 30B, 30C, and 30D illustrate two configurations of an embodiment of a bone screw according to the current invention in which said bone screws are used as anchors for a flexible vertebral support device and the bone screw having dynamically expandable side or lateral portion(s), with FIG. 30A and FIG. 30B depicting the dynamically expandable side or lateral portion(s) in a un-deployed configuration, and FIG. 30C and FIG. 30D depicting the dynamically expandable side or lateral portion(s) in a deployed configuration.

The bone screws 441G include dynamically expandable side or lateral portion(s) 432G, and optionally a distal tip 433G. FIG. 30A illustrates a side view of the bone screws 441G in a configuration prior to deployment of the dynamically expandable side or lateral portion(s) 427G and prior to deployment of distal tip 433G, following implantation within the vertebral column 435G of a subject.

Figure 30B:
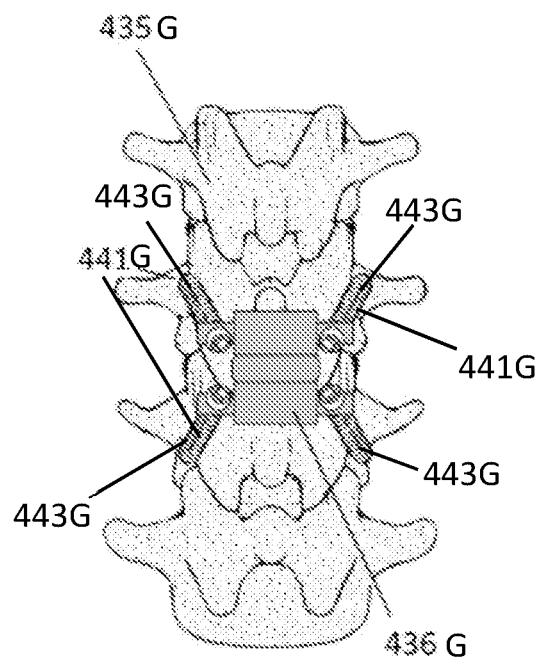
Figure 30C:
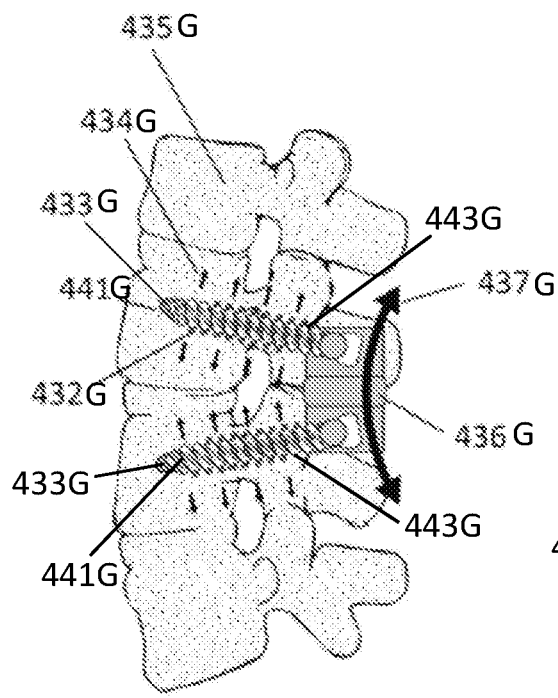
Figure 30D:
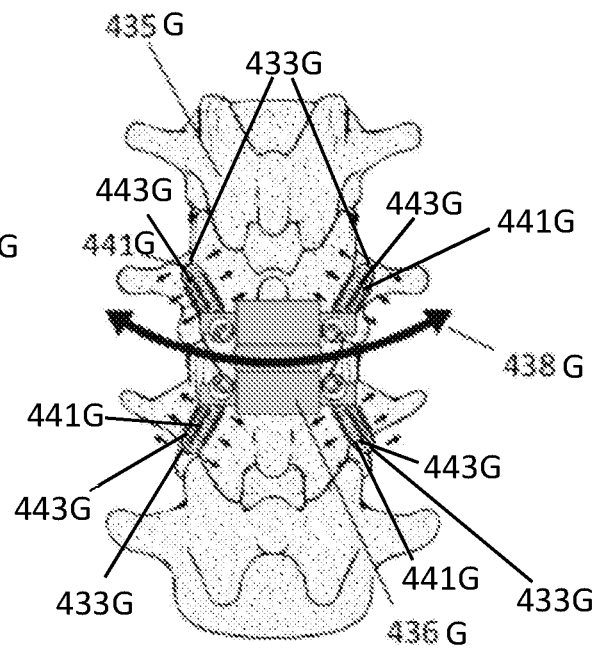

FIG. 30B illustrates the bone screws 441G in the same configuration as for FIG. 30A, as viewed from the rear of the vertebral column 435. FIG. 30C illustrates the bone screws 441G following deployment of the dynamically expandable side or lateral portion(s) 427G and prior to deployment of distal tip 433 using a mechanism such the threaded rod 412 or 421 similarly as described in FIGS. 26A-26B and FIGS. 27A-27B to urge such expandable side or lateral portion(s) 432G features outwards 434G through holes in the bone screw 441G and into the surrounding bone tissue as depicted in FIGS. 30C and 30D which are a side view and a rear view respectively. In their deployed configuration such dynamically expandable features 432G help to reduce migration and aseptic loosening of the bone screws 441G, in part by expanding into voids of the trabeculae in response to the applied load, as further illustrated in and as described in reference to FIGS. 32A-C.

The side view of FIG. 30C further illustrates one example of the type of rotational range of motion or flexion 437G that may be required for the proper function of a flexible vertebral support device 436G, as well the net reaction force exerted on the bone tissue by the dynamically expandable side or lateral portion(s) 427G in response to such rotational motion or flexion 437G by the flexible vertebral support device 436G. FIG. 30D illustrates the rear view of the bone screws 441G in the same configuration as FIG. 30C, while the flexible vertebral support device 436G undergoes another type of rotational motional or flexion 438G.

Figure 31:
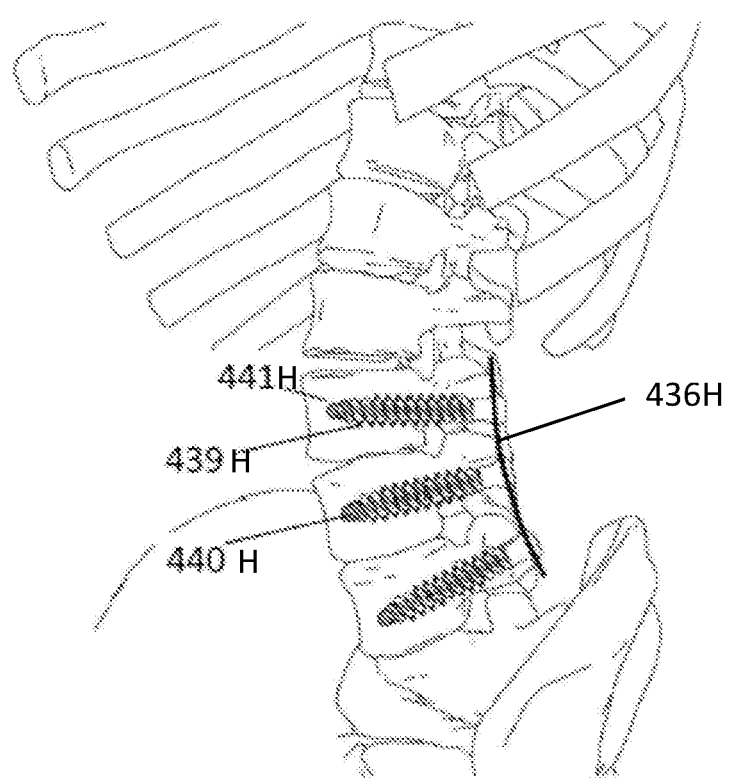
FIG. 31 illustrates a further embodiment of a bone screw of the current invention in which said bone screws are used as anchors for a spinal implant, such as a vertebral fusion device.

FIG. 31 illustrates an embodiment whereby same screws 441H of the current invention are depicted in which said bone screws 441H are used as anchors for a spinal implant, such as a vertebral fusion device 436H. The bone screws 441 include dynamically expandable side or lateral portion(s) 439H, and optionally a distal tip 440H, and core similar to what is illustrated in and described in reference to FIGS. 28A-28B and FIGS. 29A-29B.

FIG. 32A illustrates another embodiment of the current invention in the form of a bone screw 441I with dynamically expandable side or lateral portion(s) 439I and with or without dynamically expandable distal tip 440I placed in proximity to bone tissue 18I. For the purpose of illustration, an example of the porous surface 444I of such bone tissue is shown at somewhat exaggerated scale.

As shown in FIGS. 32B and 32C, physiological loading of the bone tissue, represented by arrows 442I and 443I, urges the porous surface 444I of the bone tissue towards the proximal end of the implanted fixation device which is in the present embodiment a bone screw 441I, transferring part of the load to the dynamically expandable side or lateral portion(s) 439I of the bone screw 441I. These dynamically expandable side or lateral portion(s) 439I thereby expand(s) 446I with a force and in a direction at least normal to the direction of the load 442I and 443I, increasing contact area 445I with the bone tissue 18I. Likewise, the side or lateral portions 439I expand(s) under load, such that numerous finger-like portions or projections of tip material 447I can partially occupy vacancies in the porous surface 448I, further increasing the contact area with the bone tissue and thereby resisting penetration of the bone screw 441I into the bone, which reduces migration and potential aseptic loosening.

Figures 33A, 33B:
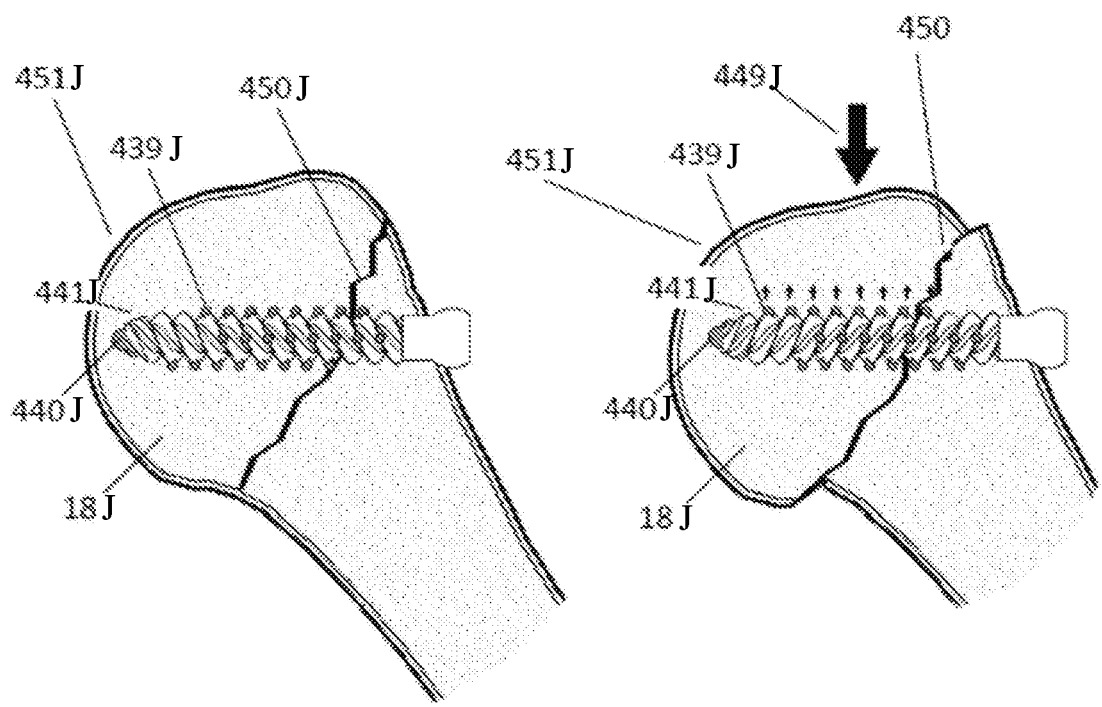
FIGS. 33A and 33B illustrate an embodiment of a fixation device of the subject invention for utilisation for fixation of a neck fracture of the proximal humerus both before FIG. 33A and during FIG. 32B compression of the screw after implantation of the bone screw in the bone.

FIGS. 33A and 33B illustrate a further embodiment of the current invention in the form of a bone screw 441J with dynamically expandable side or lateral portion(s) 439J and optionally with or without a dynamically expandable distal tip 440J placed in proximity to bone tissue 18J, for the reduction and fixation of a neck fracture 450J of the proximal humerus 451J. As shown in FIG. 33A, the bone screw 441J is within the bone tissue 18J so as to reduce the fracture 450J, and the dynamically expandable side or lateral portion(s) 439J have been deployed in a manner including those as described above in reference to other embodiments. As shown in FIG. 33B, a load 449J is imparted from physical and/or physiological loading and the dynamically expandable side or lateral portion(s) 439J of the screw 441J expand due to such loading due to a reaction force, which causes the dynamically expandable side or lateral portion(s) 439J to expand in at least a direction along the longitudinal axis of the bone screw 441J so as to oppose and resist migration of the bone screw 441J through the bone tissue 18J in accordance with the current invention.

Figure 34:
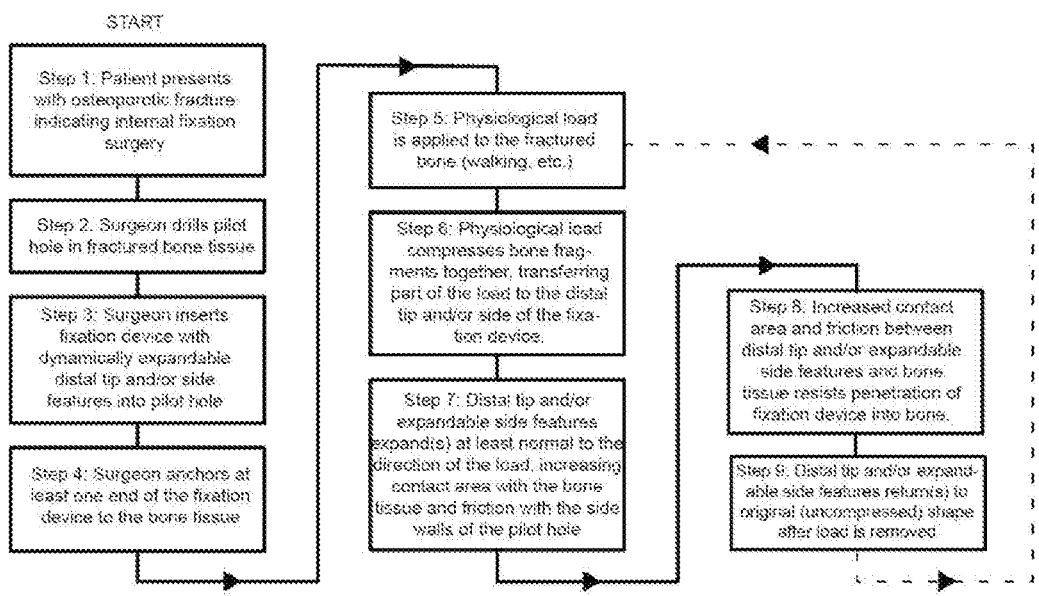
FIG. 34 shows a flowchart representing the steps of one example for the process of how the current invention, including dynamically expandable side or lateral portion(s) dynamically expandable side or lateral portion(s) and distal tip as illustrated in FIGS. 29A-29B can usefully resist bone tissue penetration following surgical implantation in a fractured bone.

FIG. 34 shows a flowchart representing the steps of one example for the process of how the current invention, including dynamically expandable side or lateral portion(s) and distal tip as illustrated in FIGS. 29A-29B of a fixation device such as a bone screw can may usefully resist bone tissue penetration following surgical implantation in a fractured bone. Such a procedure is generalized by the present flowchart example, and additional steps may be incorporated during the deployment of such a device within a subject.

Figure 35A:
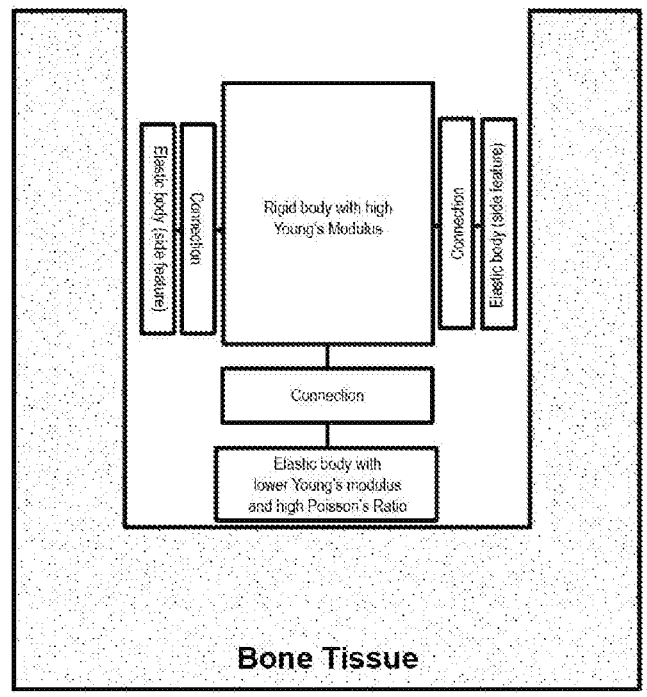
FIGS. 35A and 35B illustrate a block diagram of the essential components of an embodiment of a bone screw embodiment of the current invention.
Figure 35B:
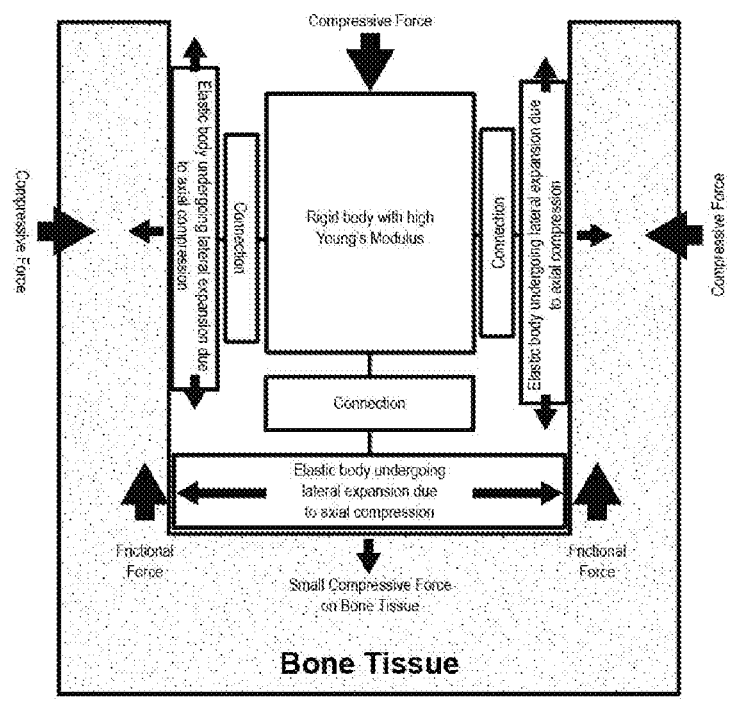

FIGS. 35A and 35B illustrate a block diagram of the essential components of one bone screw embodiment of the current invention, whereby as demonstrated by FIG. 35B, upon application of compressive forces due to physical and/or physiological loading, the dynamically expandable portions expand so as to reduce loading to adjacent bone and so as to resist migration of a device through adjacent bone tissue.

Figure 36A:
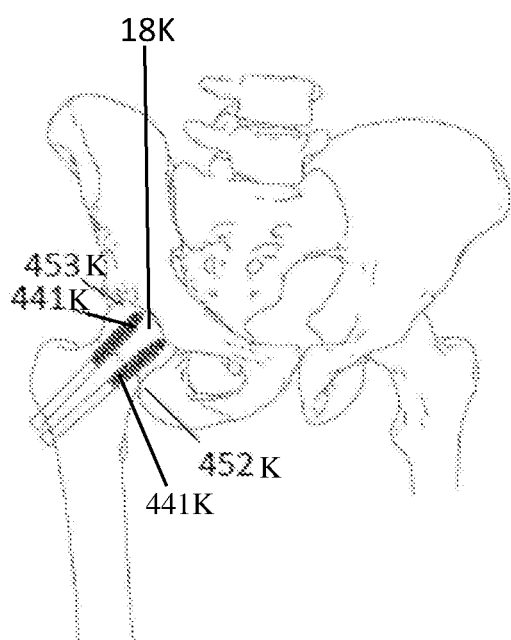
FIGS. 36A, 36B, and 36C illustrate one embodiment of the current invention used to fix fractures of the proximal femur.
Figures 36B, 36C:
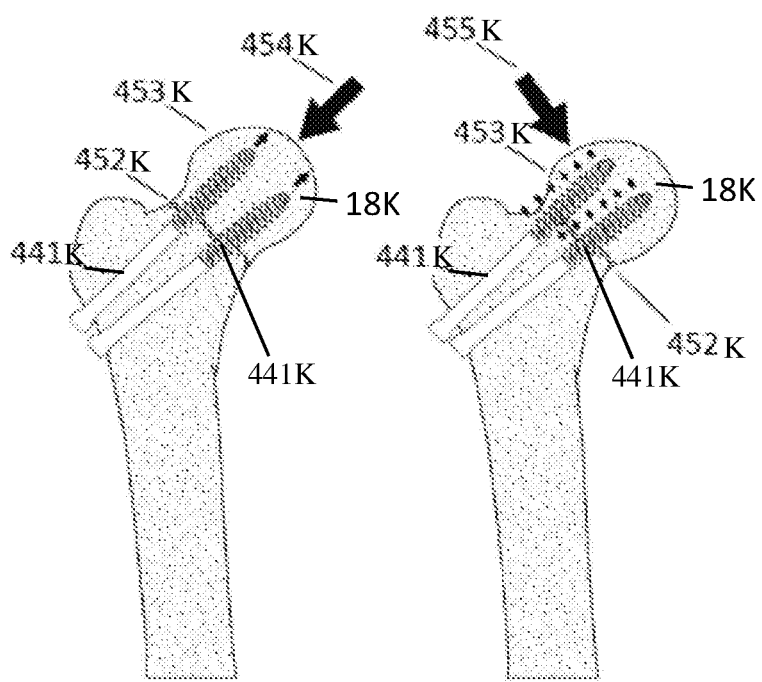

FIGS. 36A, 36B, and 36C illustrate an embodiment of the current invention in the form of a bone screw 441K having dynamically expandable side or lateral portion(s) 439K and optionally with or without dynamically expandable distal tip 440K placed in proximity to bone tissue 18K, for the reduction and fixation of a neck fracture 452K of the proximal femur 453K as shown in FIG. 36A. Referring to FIG. 36B, there is depicted axial compression 454K to the neck of the femur, and as shown in FIG. 36C there is depicted side or lateral compression 455K, of the bone screw 441K after implantation in the bone. In accordance with the current invention, the dynamically expandable side or lateral portion(s) 439K expand and the dynamically expandable distal tip 440K expands dynamic lateral and axial loads respectively so as to reduce loading to adjacent bone and so as to resist migration of the bone screw 441J through adjacent bone tissue 18J.

Example 3: Artificial Bone Penetration Test 2

Figure 37:
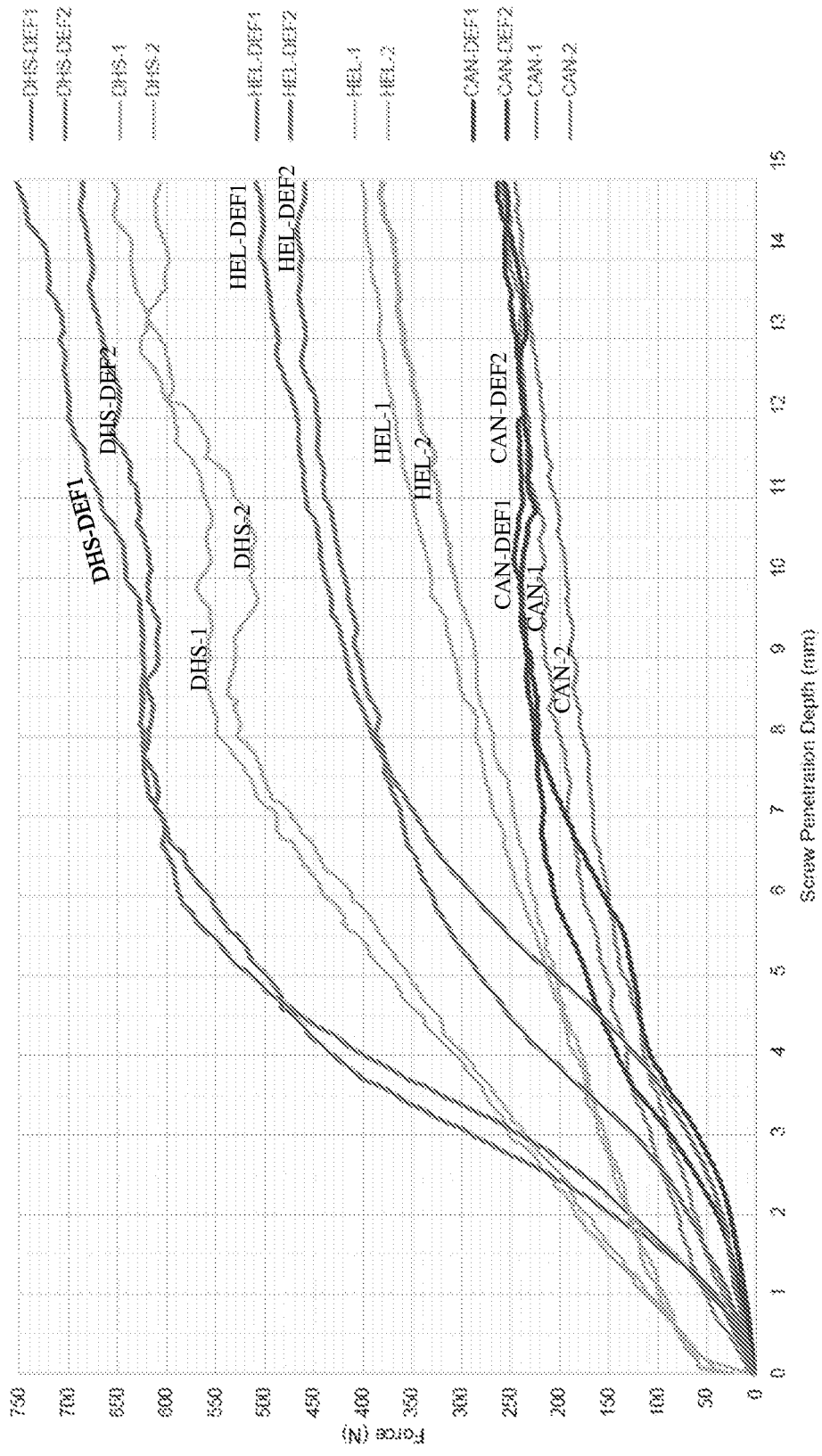
FIG. 37 represents the results of a pilot study conducted to compare the effectiveness of a typical blunt-tip stainless steel bone screw at preventing cut-out, with a prototype bone screw, according to the subject invention, having a dynamically expandable elastomeric polymer tip after implantation in artificial bone tissue made of polyurethane foam.

In FIG. 37, there is shown the results of synthetic bone tissue (Sawbones™ Type 10—0.16 g/cc rigid polyurethane foam, manufactured as a substrate for simulating the mechanical properties of human osteoporotic bone) penetration experiments, in which a comparison the rates of penetration of bone screws featuring dynamically expanding tips as provided by the current invention, with the rates of penetration of conventional bone screws, such rates of penetration being in common clinical use. These experiments, conducted by the inventors under controlled laboratory conditions based on standards detailed in ASTM F543, were utilized to determine the penetration rate of 5 mm diameter bone screws placed in shallow 6 mm diameter pilot holes drilled into the surfaces of the synthetic bone material.

Each screw type was loaded axially by use of an MTS™ a mechanical testing machine with a displacement rate of 5 millimeters per minute, until penetration of the screw through the synthetic bone was achieved (representing approximately 1.5 cm of bone penetration). The data from experiments in respect of screws with deformable, dynamically expandable tips are indicated with a "DEF" suffix in the legend.

All "DEF" screws include a 5 mm long, 5 mm diameter dynamically expandable tip of silicone rubber, 60A Shore A hardness, placed between the distal tip of the metal screw and the synthetic bone. "DHS" indicates dynamic hip screw, "HEL" indicates helical blade TFNA nail, "CAN" indicates cannulated titanium screw).

The results from this experimental study demonstrated that the inclusion of a dynamically expandable elastomer distal tip to several common clinically-useful bone screw types gave (i) a generally improved penetration resistance, and as well as a significantly greater force required, in some cases in excess of 130% such as for the DHS example, to achieve the same level of penetration, thus demonstrating an increased resistance to penetration and migration due to the utilisation of the dynamically expandable elastomer distal tip as defined by the current invention.

As is demonstrated, by the experimental results, when a dynamically expanding tip is utilized, a toe-in displacement occurs with increased displacement of the bone screw in relation to rate of load increase initially, as the dynamically expanding tip is initially compressed. However, upon such toe-in condition being achieved, which may be considered akin to pre-loading of the screw within bone, there is a marked increase in stiffness of the construct in comparison with the absence of a dynamically expanding tip. For example, for the DHS samples, at a load of 500N, a displacement of the screw of approximately 4.5 mm is achieved, whereas for a same load in the absence of a dynamically expanding tip a displacement of 7 mm results. As can be inferred from such experimental results, the presence of a dynamically expanding in accordance with to current invention for a given system loading significantly reduces the amount of movement of a screw through bone and as such, substantially reduces migration of such a screw or implant into adjacent bone tissue. Further, it is also inferred that with a lesser displacement and migration of a screw through bone tissue in the presence of a dynamically expanding tip and the expansion thereof, provides preferential distal loading to bone tissue adjacent the distal tip, which is known to stimulate bone and in the absence of stress shielding reduce the likelihood of bone resorption and detrimental effects of such physiological changes, including reduce migration and aseptic loosening.

Example 4: Artificial Bone Penetration Test 3

Figure 38:
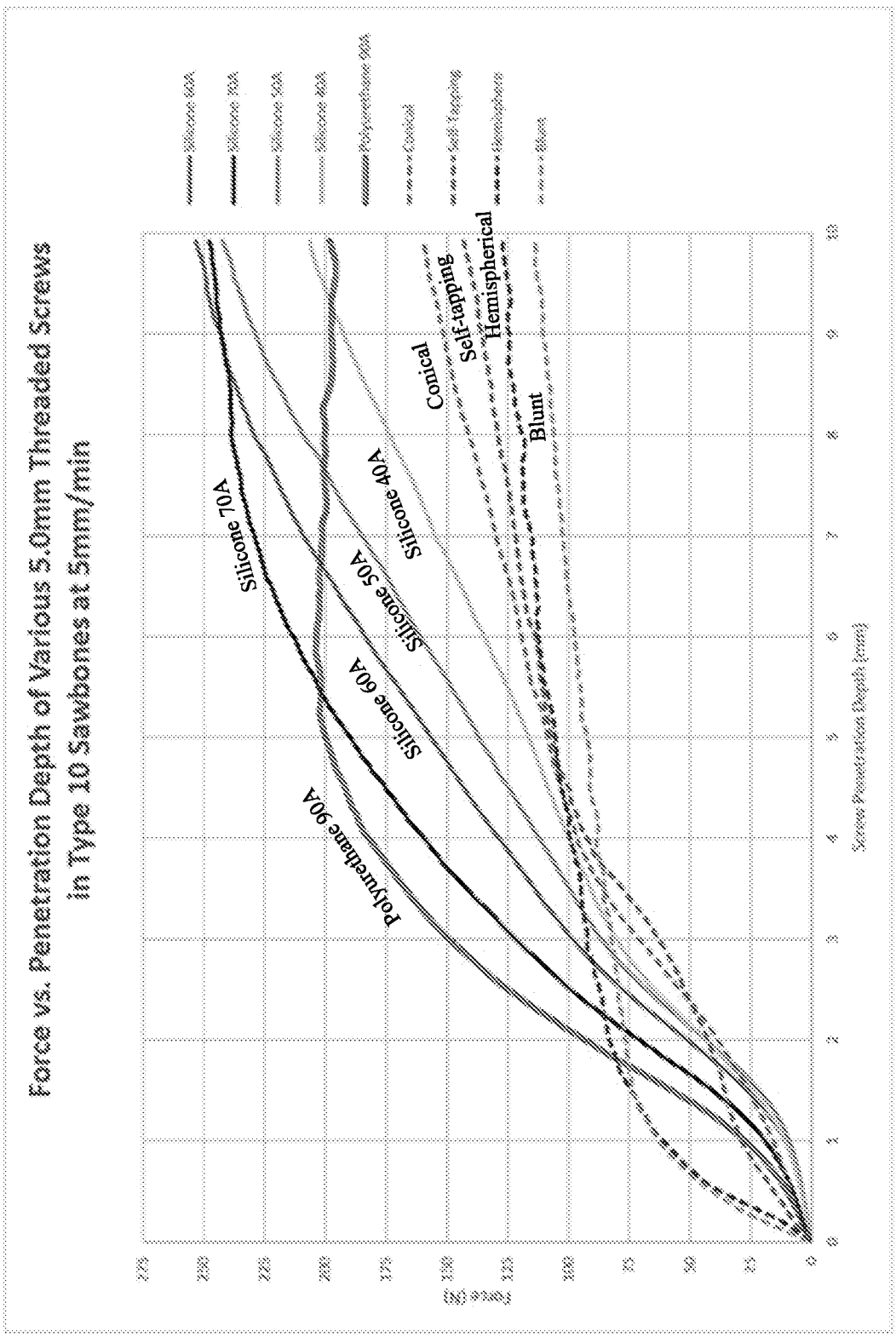
FIG. 38 represents the results of a pilot study conducted to compare the effectiveness of a typical blunt-tip stainless steel bone screw at preventing cut-out, with a prototype bone screw, according to the subject invention, having a dynamically expandable elastomeric polymer tip after implantation in artificial bone tissue made of polyurethane foam.

In FIG. 38, there is shown the results of synthetic bone tissue (Sawbones™ Type 10—0.16 g/cc rigid polyurethane foam, manufactured as a substrate for simulating the mechanical properties of human osteoporotic bone) penetration experiments, comparing the rates of penetration of bone screws including dynamically expanding tips of the current invention with the rates of penetration of conventional bone screws in common clinical use.

These experiments, conducted by the inventors under controlled laboratory conditions based on standards detailed in ASTM F543, provided for the testing of the penetration rate of 5 mm diameter bone screws placed in shallow 6 mm diameter pilot holes drilled into the surface of the synthetic bone material.

Each screw type, was loaded axially by way of an MTS™ mechanical testing machine with a displacement rate of 5 millimeters per minute, until penetration of the screw through the synthetic bone was achieved (representing approximately 1.5 cm of bone penetration).

All screws were typical stainless steel locking bone screw of 5 mm diameter. "Silicone 40A, 50A, 60A, 70A" indicate blunt tip screws with an additional 5 mm long, 5 mm diameter tip of silicone rubber of 40A, 50A, 60A, or 70A Shore A hardness between the distal tip of the metal screw and the synthetic bone. "Polyurethane 90A" indicates a blunt tip screw with a 5 mm long, 5 mm diameter tip of polyurethane rubber, 90A Shore A hardness, placed between the distal tip of the metal screw and the synthetic bone.

The results from this study demonstrate that the addition of a dynamically expandable elastomer distal tip to several common clinically-useful bone screw types increased penetration resistance, and furthermore that for osteoporotic bone, silicone rubber of hardness 60A or 70A offers the greatest improvement in penetration resistance. As such, the dynamically expandable elastomer distal tip as provided by the current invention is indicated to provide resistance to screw migration.

Similarly as demonstrated by the presence of a dynamically expanding tip as shown by the results of Experiment 3 in FIG. 37, when a dynamically expanding tip is utilized, a toe-in displacement occurs with increased displacement of the bone screw in relation to rate of load increase initially, as the dynamically expanding tip is initially compressed. However, upon such toe-in condition being achieved, there is a marked increase in stiffness of the construct in comparison with the absence of a dynamically expanding tip. The presence of a significantly greater load to provide a same amount of displacement of a screw through bone tissue in the presence of a dynamically expanding tip and the expansion thereof, may be inferred to provide preferential distal loading to bone tissue adjacent the distal tip, which is known to stimulate bone and in the absence of stress shielding reduce the likelihood of bone resorption and detrimental effects of such physiological changes, including reduce migration and aseptic loosening.

For example, for the DHS samples, at a load of 500N, a displacement of the screw of approximately 4.5 mm is achieved, whereas for a same load in the absence of a dynamically expanding tip a displacement of 7 mm results. As can be inferred from such experimental results, the presence of a dynamically expanding in accordance with to current invention for a given system loading significantly reduces the amount of movement of a screw through bone and as such, substantially reduces migration of such a screw or implant into adjacent bone tissue. Further, it is also inferred that with a lesser displacement and migration of a screw through bone tissue in the presence of a dynamically expanding tip and the expansion thereof, provides preferential distal loading to bone tissue adjacent the distal tip, which is known to stimulate bone and in the absence of stress shielding reduce the likelihood of bone resorption and detrimental effects of such physiological changes, including reduce migration and aseptic loosening.

FIG. 39 illustrates an embodiment of a bone screw 441L of the current invention with dynamically expandable side or lateral portion(s) 401L consisting of a mechanism designed to approximate the mechanical behavior of an elastomeric material such as a rubber or elastic foam.

FIGS. 40A, 40B, and 40C illustrate a further embodiment of the current invention, whereby a fixation device is provided in the form of an anchor 456M for sutures 457M, the anchor 456M with dynamically expandable side or lateral portion(s) 439M and with our without dynamically expandable distal tip placed in proximity to bone tissue 18M, for repair of repair of connective tissue, muscle, and/or other soft tissue. Such devices are often termed suture anchors within the art.

Such an anchor embodiment may be used for, but is not limited to, securing soft tissue or connective tissue repair of soft tissue injuries and reattachment of soft tissue or connective tissue to bone, such as when a tendon has become detached from bone.

For example, such an anchor 456M may be utilized for repair in the vicinity of the proximal humerus 451M, for various injuries such as rotator cuff tears and lesions, such as a Bankart lesion FIG. 40A illustrates such an anchor 456M prior to implantation in the proximal humerus 451M of a subject. FIG. 40B illustrates the anchor 456M implanted within the bone tissue 18M of the proximal humerus 451M, prior to deployment of the dynamically expandable side or lateral portion(s) 439M into the bone tissue. FIG. 40C illustrates the anchor 456M after such implantation with its dynamically expandable side or lateral portion(s) 439M in a deployed configuration. In such a deployed configuration within the bone tissue 18M, the dynamically expandable side or lateral portion(s) 439M may provide clinical benefits beyond the current state of the art in suture anchors, such as reducing the incidences and rates of aseptic loosening, stress shielding, migration of the anchor within the bone, loosening and instability of the anchor and potential pull-out, and other complications related to placement of an implant or fixation device within bone.

Referring to FIGS. 41(i) to 41(iv), there is shown an embodiment of a deformable element 12N according to the current invention, for opposing migration of a bone engagement device 10N within bone tissue 18N, in the present embodiment, the bone engagement device 10N is a bone screw which is used to secure a securement element 201N to the proximal lateral aspect of a humerus of a subject to as to provide fixation for a fracture.

In the present embodiment, the deformable element 12N is provided separately from the bone engagement device 10N, and an aperture is formed in the bone 18N so as to bridge the fracture as shown in FIG. 41(i). The deformable element 12N is then inserted into the aperture as denoted by dashed lines as shown in FIG. 41(ii) towards the distal end of the aperture. The bone engagement device 10N which is a bone screw in the present embodiment, is then inserted into the aperture and screwed in towards the deformable element 12N as shown in FIG. 41(iii). Upon the bone engagement device 10N being urged against the deformable element 12N, the deformable element 12N is urged further distally within the aperture and abuts adjacent bone tissue 204N as shown in FIG. 41(iv).

Similarly as described with other embodiments of the current invention, the deformable element 12N is sized and formed from a material such that upon being disposed between bone tissue adjacent bone tissue 204N and the bone engagement device 10N, upon adjacent bone tissue 204 being urged against the deformable element 12N, the deformable element 12N deforms in at least a direction of at least laterally in relation to the direction from which the adjacent bone tissue 204N is urged against the deformable element 12N. Deformation of the deformable element 12N causes an increased contact area between the deformable element 12N and the adjacent bone tissue 204N and a reduction in stress in the adjacent bone tissue 204N and opposes migration of the bone engagement device 10N into the adjacent bone tissue 204N.

Referring to FIGS. 42(i) to 42(iv), a further embodiment of the current invention is shown, and similarly to the embodiment of FIGS. 41(i) to 41(iv), in the present embodiment, the deformable element 12P is provided separately from the bone engagement device 10P, and an aperture is formed in the bone 18P so as to bridge the fracture as shown in FIG. 42(i). The deformable element 12P is then inserted into the aperture as denoted by dashed lines as shown in FIG. 412(ii) towards the distal end of the aperture. The bone engagement device 10P which is a bone screw in the present embodiment, is then inserted into the aperture and screwed in towards the deformable element 12P as shown in FIG. 42(iii). Upon the bone engagement device 10N being urged against the deformable element 12P, the deformable element 12P is urged further distally within the aperture and abuts adjacent bone tissue 204P as shown in FIG. 42(iv).

In the present embodiment, the deformable element 12P includes a bearing portion P458P upon which the abutment surface is provided upon which the bone engagement device 10P is urged when the bone engagement device 10N urges the deformable element 12P distally within the aperture, and when the adjacent bone tissue urges the deformable element 12P towards the bone engagement device 10P. The bearing portion is formed from a material so as to resist penetration of the bone engagement device into the deformable element. As such, the distal end of the bone engagement device 10P is prevented from tearing or corrupting the integrity of the deformable element 12P.

Throughout the description in reference to the present invention, the term "implant" is used. Such an implant includes any device for which fixation thereof within bone tissue is required. As such, the term "implant" includes devices which may be press-fit into apertures in bone or driven into bone, as well as devices having engagement portions for engagement with bone such as a screw having a screw thread. In all such cases, an "implant" is requires to be fixedly engages with bone, and may have physiological or physical loads applied thereto, the resultant of which must be resisted so as to maintain the integrity of fixation of the implant with respect to bone.

Throughout the examples, embodiments and claims, the terms utilized in respect of the expandable or deformable element of the current invention has been described as being a dynamically expandable tip, expandable portion, deformable element portion, deformable element, expandable portion features, portion features or the like, and are to be considered operably or functionally synonymous in the deformation upon loading to adjacent bone tissue cause increased contact area and load distribution, which reduces penetration of an implant and migration thereof through the adjacent bone tissue.

We claim:

1. A device for engagement with a bone of a patient, the device comprising:
   a body portion for penetration of and fixation to bone tissue, the body portion having a distal end and a proximal end;
   an engagement portion for engagement with said bone tissue; and
   a deformable element portion extending from the body portion,
   wherein the deformable element portion is sized and formed from a dynamically expandable material such that following implantation of the device into the bone tissue and upon application of compressive forces due to physical and/or physiological loading, and upon a compressive forces being applied by adjacent bone tissue to the deformable element portion from said physical and/or physiological loading, the deformable element portion deforms and expands at least laterally in relation to the direction from which the compressive force is applied by the adjacent bone tissue which is urged against the deformable element portion; and
   wherein deformation and lateral expansion of the deformable element portion causes an increased contact area between the deformable element portion and the adjacent bone tissue and a reduction in stress in the adjacent bone tissue and opposes migration of the body portion into the adjacent bone tissue.

2. The device according to claim 1, wherein the deformable element portion is operably adjacent the distal end of the body portion, such that upon adjacent bone tissue to the deformable element portion being urged against the deformable element portion the deformable element portion deforms in a direction of at least from the distal end towards the proximal end of the body portion.

3. The device according to claim 1, wherein the deformable element portion extends along at least a portion of the body portion in a direction of from the distal end towards the proximal end of the body portion such that upon adjacent bone tissue to the deformable element portion being urged against the deformable element portion in a direction of at least normal to the direction of from the distal end towards the proximal end of the body portion, the deformable element portion deforms in at least a direction of from the distal end towards the proximal end of the body portion.

4. The device according to claim 3, wherein the deformable element portion is disposed within the body portion and is deployable so as to extend in the direction of at least normal to the direction of from the distal end towards the proximal end of the body portion upon the device being engaged within the bone tissue.

5. The device according to claim 4, wherein the body portion includes a passage therein extending in a direction of from the proximal end towards the distal end of the body portion and a plurality of apertures providing communication from said passage to external of the body portion, wherein the deformable element portion is deployable from within the passage of the body portion so as to extend in the direction of at least normal from the direction of from the proximal end towards the distal end of the body portion.

6. The device according to claim 5, wherein the deformable element portion is deployable by way of being urged through said apertures by urging a deployment into the passage of the body portion from the proximal end of the body portion.

7. The device according to claim 3, wherein the body portion includes a thread portion extending about an axis of the body portion of from the proximal end towards the distal end for engagement with the bone tissue.

8. The device according to claim 3, wherein the body portion includes a passage therein extending in a direction of from the proximal end towards the distal end of the body portion and a plurality of apertures providing communication from said passage to external of the body portion, wherein the deformable element portion is provided as a settable material is deployable from within the passage of the body portion so as to extend in the direction of at least normal from the direction of from the proximal end towards the distal end of the body portion, and wherein the settable material in introduced into said passage from the proximal end of the body portion.

9. The device according to claim 3, further comprising a further deformable element portion adjacent the distal end of the body portion, the deformable element portion being sized and formed from a material such that upon adjacent bone tissue to the deformable element portion being urged against the deformable element portion in a direction of at least from the distal end towards the proximal end of the body portion, the deformable element portion deforms in at least a normal direction with respect to the direction of from the distal end towards the proximal end of the body portion, longitudinal axis of the body portion, and wherein deformation of the deformable element portion causes an increased contact area between the deformable element portion and the adjacent bone tissue and a reduction in stress in the adjacent bone tissue.

10. The device according to claim 1, wherein the deformable element portion is a separate element from the body portion, so as to allow delivery of the deformable element portion into an aperture in bone material prior to penetration of the body portion.

11. The device according to claim 1 wherein the deformable element portion is provided as a settable material, so as to allow the deformable element portion to be delivered into an aperture in bone material in a non-formed state, prior to penetration of the body portion.

12. The device according to claim 1, wherein the deformable element portion is formed from an elastomeric material, a rubberized material, or formed from Polydimethylsiloxane (PDMS).

13. The device according to claim 1, wherein the deformable element portion is formed from an elastically deformable material such that upon a reduction in force urging adjacent bone tissue to the deformable element portion being urged against the deformable element portion, the elasticity of the deformable element portion urges the deformable element portion towards its non-deformed state.

14. The device according to claim 1, wherein the deformable element portion is formed from a material such that upon deformation of the deformable element portion the deformable element portion is deformed and extends into pores and cavities present in adjacent bone tissue so as to further increase the contact area between the deformable element portion and the adjacent bone tissue.

15. The device according to claim 1, wherein the device is a device including a screw type fixation device, a pedicle screw or a suture anchor.

16. A system for providing control of movement of a first bone portion relative to a second bone portion, the system comprising:
   two or more devices according to claim 1, whereby at least one first device being for engagement with the first bone portion and at least one second device being for engagement with the second bone portion; and
   one or more support devices, wherein the support device is engageable with a proximal end portion of a first device and is engageable with a proximal end portion of a second device;
   wherein upon engagement of the first device with the first bone portion, upon engagement of the second device with the second bone portion and upon engagement of the support device with the proximal end portion of the first device and with the proximal end portion of the second device, control of movement is provided between the first bone portion and the second bone portion.

17. The system according to claim 16, wherein the support device provides controlled movement of the first bone portion relative to the second bone portion, or provides restriction of movement of the first bone portion relative to the second bone portion.

18. The system according to claim 16, wherein the support device is elastically deformable.

19. The system according to claim 16, wherein the support device provides controlled fixation of the first bone portion relative to the second bone portion.

20. The system according to claim 16, wherein the support device provides fixation of the first bone portion relative to the second bone portion.

* * * * *